US011299724B2

(12) United States Patent
Dukhovlinov et al.

(10) Patent No.: US 11,299,724 B2
(45) Date of Patent: Apr. 12, 2022

(54) FUSION PROTEIN, POLYNUCLEOTIDE, GENETIC CONSTRUCT, PRODUCER, PREPARATION FOR REGENERATION OF CARTILAGE

(71) Applicant: LIMITED LIABILITY COMPANY BIOCHEMICAL AGENT, St. Petersburg (RU)

(72) Inventors: Ilya Vladimirovich Dukhovlinov, St. Petersburg (RU); Ekaterina Alekseevna Fedorova, St. Petersburg (RU)

(73) Assignee: LIMITED LIABILITY COMPANY BIOCHEMICAL AGENT, St. Petersburg (RU)

( * ) Notice: Subject to any disclaimer, the term of this patent is extended or adjusted under 35 U.S.C. 154(b) by 0 days.

(21) Appl. No.: 16/316,254

(22) PCT Filed: Jul. 13, 2017

(86) PCT No.: PCT/RU2017/000521
§ 371 (c)(1),
(2) Date: Jan. 8, 2019

(87) PCT Pub. No.: WO2018/013013
PCT Pub. Date: Jan. 18, 2018

(65) Prior Publication Data
US 2019/0218539 A1 Jul. 18, 2019

(30) Foreign Application Priority Data
Jul. 14, 2016 (EA) .................. 201600575

(51) Int. Cl.
*A61K 38/00* (2006.01)
*C07K 14/485* (2006.01)
*C07K 14/495* (2006.01)
*C07K 14/50* (2006.01)
*C07K 14/65* (2006.01)
*C07K 7/08* (2006.01)
*C12N 15/62* (2006.01)
*A61P 19/02* (2006.01)
*C12N 9/72* (2006.01)
*C07K 14/79* (2006.01)
*C07K 14/475* (2006.01)

(52) U.S. Cl.
CPC ............ *C12N 9/6459* (2013.01); *A61P 19/02* (2018.01); *C07K 7/08* (2013.01); *C07K 14/475* (2013.01); *C07K 14/485* (2013.01); *C07K 14/495* (2013.01); *C07K 14/50* (2013.01); *C07K 14/503* (2013.01); *C07K 14/65* (2013.01); *C07K 14/79* (2013.01); *C12N 15/62* (2013.01); *A61K 38/00* (2013.01); *C07K 2319/02* (2013.01); *C07K 2319/30* (2013.01); *C07K 2319/33* (2013.01); *C07K 2319/70* (2013.01)

(58) Field of Classification Search
CPC ................ C07K 14/475; C07K 14/485; C07K 14/495; C07K 14/50; C07K 14/65; C07K 7/08; C07K 2319/33; C07K 2319/70; C07K 2319/30; A61K 38/18; A61K 38/10
See application file for complete search history.

(56) References Cited

U.S. PATENT DOCUMENTS

| 4,546,082 | A | 10/1985 | Kurjan et al. |
|---|---|---|---|
| 8,173,860 | B2 | 5/2012 | Meade et al. |
| 8,932,589 | B2 | 1/2015 | Glass et al. |
| 9,133,259 | B2 | 9/2015 | Haudenschild et al. |
| 2007/0286843 | A1* | 12/2007 | Pfizenmaier ............ A61P 31/00 424/93.1 |
| 2008/0138323 | A1* | 6/2008 | Lee ...................... C12N 5/0619 424/93.7 |

(Continued)

FOREIGN PATENT DOCUMENTS

| CN | 101891803 A | * 11/2010 |
|---|---|---|
| DE | 361483 | 10/1922 |
| EP | 116201 A1 | 8/1984 |

(Continued)

OTHER PUBLICATIONS

Bujia et al., Acta Otolaryngol., 1994, vol. 114(5):539-543 (abstract).*
Kuznetsov S.B. et al. Genetic markers of idiopathic and congenital scoliosis, and diagnosis of susceptibility to the disease: Review of the literature, Hirurgia Pozvonochnica, 2015, vol. 12, No. I, p. 27-35.
N.S. Kosinskaya, Developmental disorders of bone and articular apparatus, ed.Medicine, 1966 multi-volume manual of surgery, edited by V. V. Petrovsky, V. 5, Moscow-Leningrad, 1960.
Zupanets I. A., et al "[Experimental study of the effect of glucosamine hydrochloride on metabolic and repair processes in connective tissue structures]" Eksp Klin Farmakol. Nov.-Dec. 2002;65(6):67-9.

(Continued)

*Primary Examiner* — Xiaozhen Xie
(74) *Attorney, Agent, or Firm* — The Roy Gross Law Firm, LLC; Roy Gross

(57) ABSTRACT

The invention relates to molecular biology, biotechnology, medicine, veterinary science. A group of inventions is proposed: a fusion protein comprising a ligand to MATN1 protein, and a growth factor of EGF, TGF, FGF, IGF, connected via a flexible link; such fusion protein further comprising the Fc-fragment of an antibody or a polypeptide binding with FcRn and/or transferrin or a fragment thereof, connected via a flexible link; encoding polynucleotide, a genetic construct for the synthesis of the fusion protein in producer cells, or cells of a target organism, the fusion protein producer, a producer of the genetic construct, a preparation for the regeneration of cartilage containing at least 1 fusion protein or genetic construct, for parenteral or, in the case of the preparation based on at least 1 fusion protein containing the transport domain, —oral administration, in the latter case the preparation is enclosed in an enteric coating.

6 Claims, No Drawings

Specification includes a Sequence Listing.

(56) References Cited

U.S. PATENT DOCUMENTS

2011/0092677 A1    4/2011  Sadeghi et al.

FOREIGN PATENT DOCUMENTS

| | | | |
|---|---|---|---|
| EP | 123289 | | 10/1984 |
| EP | 123294 | A1 | 10/1984 |
| EP | 123544 | A1 | 10/1984 |
| EP | 163529 | | 12/1985 |
| RU | 2143495 | | 12/1999 |
| RU | 2198179 | | 2/2003 |
| RU | 2489423 | C2 | 3/2010 |
| RU | 2490278 | C2 | 1/2012 |
| RU | 2555532 | C2 | 12/2012 |
| RU | 2562232 | C2 | 12/2012 |
| WO | 200104625 | A2 | 1/2001 |
| WO | 200406260 | A1 | 1/2004 |
| WO | 2004020404 | A1 | 3/2004 |
| WO | 201211645 | A1 | 1/2012 |
| WO | 201217096 | A1 | 2/2012 |
| WO | 2013059885 | A3 | 5/2013 |
| WO | WO-2013082563 | A1 * | 6/2013 ............... A61P 3/10 |
| WO | 2015035395 | A1 | 3/2015 |
| WO | 2015070014 | A1 | 5/2015 |

OTHER PUBLICATIONS

MATN1 matrilin 1 [ *Homo sapiens* (human) ], https://www.ncbi.nlm.nih.gov/gene?Db=gene&Cmd=ShowDetailView&TermToSearch=4146, retrieved Nov. 5, 2019.
Montanaro L. et al., "Evidence of a linkage between matrilin-1 gene (MATN1) and idiopathic scoliosis". Scoliosis 1:21, 2006.
Dawson JP et al. "Epidermal growth factor receptor dimerization and activation require ligand-induced conformational changes in the dimer interface", Mol. Cell. Biol. 25: 17, 2005.
Franken Romy et al., "Circulating transforming growth factor-{beta} in Marfan syndrome". Circulation 120 (6): 526-32, 2005.
Developmental Signals—Fibroblast Growth Factor, https://embryology.med.unsw.edu.au/embryology/index.php/Developmental_Signals_-_Fibroblast_Growth_Factor, retrieved Nov. 30, 2019.
Meyer N.A. et al. "Combined insulin-like growth factor-1 and growth hormone improves weight loss and wound healing in burned rats." J Trauma. Dec. 1996;41(6):1008-12.
Martin, P. "Wound Healing—Aiming for Perfect Skin Regeneration" 1997. Science 276: 75-81. 1997.
Steenfos H. 1994. Scand J Plast Reconstr Hand Surg 28: 95-105.
Pierre et al. "Insulin-like Growth Factor-I Liposomal Gene Transfer and Systemic Growth Hormone Stimulate Wound Healing" 1997. J Burn Care Rehab 18 (4): 287-291.
Nakamura Y, Gojobori T, Ikemura T. Codon usage tabulated from international DNA sequence databases: status for the year 2000. Nucleic Acids Res. Jan. 1, 2000,28(1):292.
Kapp L. D., Lorsch J. R. The molecular mechanics of eukaryotic translation // Annual Review of Biochemistry 73/2004, 657-704.
Kozak M. (1986) "Point mutations define a sequence flanking the AUG initiator codon that modulates translation by eukaryotic ribosomes", Cell 44, 283-292.
Kozak M. Recognition of AUG and alternative initiator codons is augmented by G in position +4 but is not generally affected by the nucleotides in positions +5 and +6. EMBO J. 1997;16(9):2482-2492.
Kapila J, Rycke RD, Van Montagu M, Agenon G (1997) An Agrobacterium-mediated transient gene expression system for intact leaves. Plant Sci 122: 101-108.
Stiefel, V., Ruiz-Avila, L., Raz, R., Valles, M.P., Ghez, J., Pages, M., Martinez-Izquierdo, J.A., Ludevid, M.D., Langdale, J.A., Nelson, T., and Puigdoménech, P. (1990). Expression of a maize cell wall hydroxyproline-rich glycoprotein gene in early leaf and root vascular differentiation. Plant Cell 2, 785-793.
Hartikka J, Sawdey M, Cornefert-Jensen F, Margalith M, Barnhart K, Nolasco M, Vahlsing HL, Meek J, Marquet M, Hobart P, Norman J, Manthorpe M. An improved plasmid DNA expression vector for direct injection into skeletal muscle. Hum Gene Ther. Jun. 20, 1996;7(10):1205-17.
"Cloning Vectors", ed. Pouwls et al., Elsevier, Amsterdam—New York—Oxford, 1985, ISBN 0 444 904018.
Williams JA, Games AE, Hodgson CP. Plasmid DNA vaccine vector design: impact on efficacy, safety and upstream production. Biotechnol Adv. Jul.-Aug. 2009;27(4):353-70. doi: 10.1016/j.biotechadv.2009.02.003. Epub Feb. 20, 2009.
Studier "Protein production by auto-induction in high density shaking cultures" Protein Expr Purif. May 2005;41(1):207-34.
Komarova T. V., Skulachev M. V., Zvereva A. S., Schwartz M. A., Dorokhov Y. L., Atabekov I. G. (2006) A new virus-vector for efficient production of target proteins in plants. Biochemistry, 71(8), 1043-1049).
Kleinau S. "Adjuvant oils induce arthritis in the DA rat. I. Characterization of the disease and evidence for an immunological involvement", Journal of Autoimmunity vol. 4, Issue 6, Dec. 1991, pp. 871-880.
Gromyko, Gritsuk 2012.

* cited by examiner

```
                             SEQUENCE LISTING

<160> NUMBER OF SEQ ID NOS: 11

<210> SEQ ID NO 1
<211> LENGTH: 12
<212> TYPE: PRT
<213> ORGANISM: Artificial sequence
<220> FEATURE:
<223> OTHER INFORMATION: ligand to MATN1 protein

<400> SEQUENCE: 1

Asp Trp Arg Val Ile Ile Pro Pro Arg Pro Ser Ala
1               5                   10

<210> SEQ ID NO 2
<211> LENGTH: 53
<212> TYPE: PRT
<213> ORGANISM: Homo sapiens
<220> FEATURE:
<223> OTHER INFORMATION: EGF

<400> SEQUENCE: 2

Asn Ser Asp Ser Glu Cys Pro Leu Ser His Asp Gly Tyr Cys Leu His
1               5                   10                  15

Asp Gly Val Cys Met Tyr Ile Glu Ala Leu Asp Lys Tyr Ala Cys Asn
            20                  25                  30

Cys Val Val Gly Tyr Ile Gly Glu Arg Cys Gln Tyr Arg Asp Leu Lys
        35                  40                  45

Trp Trp Glu Leu Arg
    50

<210> SEQ ID NO 3
<211> LENGTH: 112
<212> TYPE: PRT
<213> ORGANISM: Homo sapiens
<220> FEATURE:
<223> OTHER INFORMATION: TGF?1

<400> SEQUENCE: 3

Ala Leu Asp Thr Asn Tyr Cys Phe Ser Ser Thr Glu Lys Asn Cys Cys
1               5                   10                  15

Val Arg Gln Leu Tyr Ile Asp Phe Arg Lys Asp Leu Gly Trp Lys Trp
            20                  25                  30

Ile His Glu Pro Lys Gly Tyr His Ala Asn Phe Cys Leu Gly Pro Cys
        35                  40                  45

Pro Tyr Ile Trp Ser Leu Asp Thr Gln Tyr Ser Lys Val Leu Ala Leu
    50                  55                  60

Tyr Asn Gln His Asn Pro Gly Ala Ser Ala Ala Pro Cys Cys Val Pro
65                  70                  75                  80

Gln Ala Leu Glu Pro Leu Pro Ile Val Tyr Tyr Val Gly Arg Lys Pro
                85                  90                  95

Lys Val Glu Gln Leu Ser Asn Met Ile Val Arg Ser Cys Lys Cys Ser
            100                 105                 110

<210> SEQ ID NO 4
<211> LENGTH: 123
<212> TYPE: PRT
<213> ORGANISM: Homo sapiens
<220> FEATURE:
```

<223> OTHER INFORMATION: FGF2

<400> SEQUENCE: 4

Lys Arg Leu Tyr Cys Lys Asn Gly Gly Phe Phe Leu Arg Ile His Pro
1               5                   10                  15

Asp Gly Arg Val Asp Gly Val Arg Glu Lys Ser Asp Pro His Ile Lys
            20                  25                  30

Leu Gln Leu Gln Ala Glu Glu Arg Gly Val Val Ser Ile Lys Gly Val
        35                  40                  45

Cys Ala Asn Arg Tyr Leu Ala Met Lys Glu Asp Gly Arg Leu Leu Ala
    50                  55                  60

Ser Lys Cys Val Thr Asp Glu Cys Phe Phe Phe Glu Arg Leu Glu Ser
65                  70                  75                  80

Asn Asn Tyr Asn Thr Tyr Arg Ser Arg Lys Tyr Thr Ser Trp Tyr Val
                85                  90                  95

Ala Leu Lys Arg Thr Gly Gln Tyr Lys Leu Gly Ser Lys Thr Gly Pro
            100                 105                 110

Gly Gln Lys Ala Ile Leu Phe Leu Pro Met Ser
        115                 120

<210> SEQ ID NO 5
<211> LENGTH: 153
<212> TYPE: PRT
<213> ORGANISM: Homo sapiens
<220> FEATURE:
<223> OTHER INFORMATION: IGF-1

<400> SEQUENCE: 5

Met Gly Lys Ile Ser Ser Leu Pro Thr Gln Leu Phe Lys Cys Cys Phe
1               5                   10                  15

Cys Asp Phe Leu Lys Val Lys Met His Thr Met Ser Ser Ser His Leu
            20                  25                  30

Phe Tyr Leu Ala Leu Cys Leu Leu Thr Phe Thr Ser Ser Ala Thr Ala
        35                  40                  45

Gly Pro Glu Thr Leu Cys Gly Ala Glu Leu Val Asp Ala Leu Gln Phe
    50                  55                  60

Val Cys Gly Asp Arg Gly Phe Tyr Phe Asn Lys Pro Thr Gly Tyr Gly
65                  70                  75                  80

Ser Ser Ser Arg Arg Ala Pro Gln Thr Gly Ile Val Asp Glu Cys Cys
                85                  90                  95

Phe Arg Ser Cys Asp Leu Arg Arg Leu Glu Met Tyr Cys Ala Pro Leu
            100                 105                 110

Lys Pro Ala Lys Ser Ala Arg Ser Val Arg Ala Gln Arg His Thr Asp
        115                 120                 125

Met Pro Lys Thr Gln Lys Glu Val His Leu Lys Asn Ala Ser Arg Gly
    130                 135                 140

Ser Ala Gly Asn Lys Asn Tyr Arg Met
145                 150

<210> SEQ ID NO 6
<211> LENGTH: 12
<212> TYPE: PRT
<213> ORGANISM: Artificial sequence
<220> FEATURE:
<223> OTHER INFORMATION: flexible hinge

<400> SEQUENCE: 6

Gly Gly Gly Ser Gly Gly Gly Ser Gly Gly Gly Ser
1               5                   10

<210> SEQ ID NO 7
<211> LENGTH: 227
<212> TYPE: PRT
<213> ORGANISM: Homo sapiens
<220> FEATURE:
<223> OTHER INFORMATION: Fc-fragment of an antibody

<400> SEQUENCE: 7

Asp Lys Thr His Thr Cys Pro Pro Cys Pro Ala Pro Glu Leu Leu Gly
1               5                   10                  15

Gly Pro Ser Val Phe Leu Phe Pro Pro Lys Pro Lys Asp Thr Leu Met
                20                  25                  30

Ile Ser Arg Thr Pro Glu Val Thr Cys Val Val Val Asp Val Ser His
            35                  40                  45

Glu Asp Pro Glu Val Lys Phe Asn Trp Tyr Val Asp Gly Val Glu Val
        50                  55                  60

His Asn Ala Lys Thr Lys Pro Arg Glu Glu Gln Tyr Asn Ser Thr Tyr
65                  70                  75                  80

Arg Val Val Ser Val Leu Thr Val Leu His Gln Asp Trp Leu Asn Gly
                85                  90                  95

Lys Glu Tyr Lys Cys Lys Val Ser Asn Lys Ala Leu Pro Ala Pro Ile
            100                 105                 110

Glu Lys Thr Ile Ser Lys Ala Lys Gly Gln Pro Arg Glu Pro Gln Val
        115                 120                 125

Tyr Thr Leu Pro Pro Ser Arg Glu Glu Met Thr Lys Asn Gln Val Ser
130                 135                 140

Leu Thr Cys Leu Val Lys Gly Phe Tyr Pro Ser Asp Ile Ala Val Glu
145                 150                 155                 160

Trp Glu Ser Asn Gly Gln Pro Glu Asn Asn Tyr Lys Thr Thr Pro Pro
                165                 170                 175

Val Leu Asp Ser Asp Gly Ser Phe Phe Leu Tyr Ser Lys Leu Thr Val
            180                 185                 190

Asp Lys Ser Arg Trp Gln Gln Gly Asn Val Phe Ser Cys Ser Val Met
        195                 200                 205

His Glu Ala Leu His Asn His Tyr Thr Gln Lys Ser Leu Ser Leu Ser
    210                 215                 220

Pro Gly Lys
225

<210> SEQ ID NO 8
<211> LENGTH: 37
<212> TYPE: PRT
<213> ORGANISM: Artificial sequence
<220> FEATURE:
<223> OTHER INFORMATION: polypeptide binding with FcRn

<400> SEQUENCE: 8

Val Asp Ala Lys Tyr Ala Lys Glu Ile Arg Trp Leu Pro Asn Leu Asp
1               5                   10                  15

Pro Ser Gln Ser Ser Glu Leu Leu Ala Glu Ala Lys Lys Leu Asn Asp
                20                  25                  30

Ser Gln Ala Pro Lys
            35

<210> SEQ ID NO 9
<211> LENGTH: 697
<212> TYPE: PRT
<213> ORGANISM: Homo sapiens
<220> FEATURE:
<223> OTHER INFORMATION: transferrin

<400> SEQUENCE: 9

```
Arg Leu Ala Val Gly Ala Leu Leu Val Cys Ala Val Leu Gly Leu Cys
1               5                   10                  15

Leu Ala Val Pro Asp Lys Thr Val Arg Trp Cys Ala Val Ser Glu His
                20                  25                  30

Glu Ala Thr Lys Cys Gln Ser Phe Arg Asp His Met Lys Ser Val Ile
            35                  40                  45

Pro Ser Asp Gly Pro Ser Val Ala Cys Val Lys Ala Ser Tyr Leu
        50                  55                  60

Asp Cys Ile Arg Ala Ile Ala Ala Asn Glu Ala Asp Ala Val Thr Leu
65                  70                  75                  80

Asp Ala Gly Leu Val Tyr Asp Ala Tyr Leu Ala Pro Asn Asn Leu Lys
                85                  90                  95

Pro Val Val Ala Glu Phe Tyr Gly Ser Lys Glu Asp Pro Gln Thr Phe
                100                 105                 110

Tyr Tyr Ala Val Ala Val Val Lys Lys Asp Ser Gly Phe Gln Met Asn
            115                 120                 125

Gln Leu Arg Gly Lys Lys Ser Cys His Thr Gly Leu Gly Arg Ser Ala
        130                 135                 140

Gly Trp Asn Ile Pro Ile Gly Leu Leu Tyr Cys Asp Leu Pro Glu Pro
145                 150                 155                 160

Arg Lys Pro Leu Glu Lys Ala Val Ala Asn Phe Phe Ser Gly Ser Cys
                165                 170                 175

Ala Pro Cys Ala Asp Gly Thr Asp Phe Pro Gln Leu Cys Gln Leu Cys
            180                 185                 190

Pro Gly Cys Gly Cys Ser Thr Leu Asn Gln Tyr Phe Gly Tyr Ser Gly
        195                 200                 205

Ala Phe Lys Cys Leu Lys Asp Gly Ala Gly Asp Val Ala Phe Val Lys
    210                 215                 220

His Ser Thr Ile Phe Glu Asn Leu Ala Asn Lys Ala Asp Arg Asp Gln
225                 230                 235                 240

Tyr Glu Leu Leu Cys Leu Asp Asn Thr Arg Lys Pro Val Asp Glu Tyr
                245                 250                 255

Lys Asp Cys His Leu Ala Gln Val Pro Ser His Thr Val Val Ala Arg
            260                 265                 270

Ser Met Gly Gly Lys Glu Asp Leu Ile Trp Glu Leu Leu Asn Gln Ala
        275                 280                 285

Gln Glu His Phe Gly Lys Asp Lys Ser Lys Glu Phe Gln Leu Phe Ser
    290                 295                 300

Ser Pro His Gly Lys Asp Leu Leu Phe Lys Asp Ser Ala His Gly Phe
305                 310                 315                 320

Leu Lys Val Pro Pro Arg Met Asp Ala Lys Met Tyr Leu Gly Tyr Glu
                325                 330                 335

Tyr Val Thr Ala Ile Arg Asn Leu Arg Glu Gly Thr Cys Pro Glu Ala
            340                 345                 350

Pro Thr Asp Glu Cys Lys Pro Val Lys Trp Cys Ala Leu Ser His His
        355                 360                 365
```

Glu Arg Leu Lys Cys Asp Glu Trp Ser Val Asn Ser Gly Lys Ile
    370                 375                 380

Glu Cys Val Ser Ala Glu Thr Thr Glu Asp Cys Ile Ala Lys Ile Met
385                 390                 395                 400

Asn Gly Glu Ala Asp Ala Met Ser Leu Asp Gly Gly Phe Val Tyr Ile
                405                 410                 415

Ala Gly Lys Cys Gly Leu Val Pro Val Leu Ala Glu Asn Tyr Asn Lys
            420                 425                 430

Ser Asp Asn Cys Glu Asp Thr Pro Glu Ala Gly Tyr Phe Ala Val Ala
            435                 440                 445

Val Val Lys Lys Ser Ala Ser Asp Leu Thr Trp Asp Asn Leu Lys Gly
    450                 455                 460

Lys Lys Ser Cys His Thr Ala Val Gly Arg Thr Ala Gly Trp Asn Ile
465                 470                 475                 480

Pro Met Gly Leu Leu Tyr Asn Lys Ile Asn His Cys Arg Phe Asp Glu
                485                 490                 495

Phe Phe Ser Glu Gly Cys Ala Pro Gly Ser Lys Lys Asp Ser Ser Leu
                500                 505                 510

Cys Lys Leu Cys Met Gly Ser Gly Leu Asn Leu Cys Glu Pro Asn Asn
            515                 520                 525

Lys Glu Gly Tyr Tyr Gly Tyr Thr Gly Ala Phe Arg Cys Leu Val Glu
            530                 535                 540

Lys Gly Asp Val Ala Phe Val Lys His Gln Thr Val Pro Gln Asn Thr
545                 550                 555                 560

Gly Gly Lys Asn Pro Asp Pro Trp Ala Lys Asn Leu Asn Glu Lys Asp
                565                 570                 575

Tyr Glu Leu Leu Cys Leu Asp Gly Thr Arg Lys Pro Val Glu Glu Tyr
                580                 585                 590

Ala Asn Cys His Leu Ala Arg Ala Pro Asn His Ala Val Val Thr Arg
            595                 600                 605

Lys Asp Lys Glu Ala Cys Val His Lys Ile Leu Arg Gln Gln Gln His
    610                 615                 620

Leu Phe Gly Ser Asn Val Thr Asp Cys Ser Gly Asn Phe Cys Leu Phe
625                 630                 635                 640

Arg Ser Glu Thr Lys Asp Leu Leu Phe Arg Asp Asp Thr Val Cys Leu
                645                 650                 655

Ala Lys Leu His Asp Arg Asn Thr Tyr Glu Lys Tyr Leu Gly Glu Glu
            660                 665                 670

Tyr Val Lys Ala Val Gly Asn Leu Arg Lys Cys Ser Thr Ser Ser Leu
    675                 680                 685

Leu Glu Ala Cys Thr Phe Arg Arg Pro
    690                 695

<210> SEQ ID NO 10
<211> LENGTH: 15
<212> TYPE: PRT
<213> ORGANISM: Artificial sequence
<220> FEATURE:
<223> OTHER INFORMATION: transferrin fragment

<400> SEQUENCE: 10

Thr His Arg Pro Pro Met Trp Ser Pro Val Trp Pro Gly Gly Gly
1               5                   10                  15

<210> SEQ ID NO 11

```
<211> LENGTH: 136
<212> TYPE: PRT
<213> ORGANISM: Artificial sequence
<220> FEATURE:
<223> OTHER INFORMATION: example of components link in a fusion protein,
      SEQ ID NO:3-SEQ ID NO:6-SEQ ID NO:1

<400> SEQUENCE: 11

Ala Leu Asp Thr Asn Tyr Cys Phe Ser Ser Thr Glu Lys Asn Cys Cys
1               5                   10                  15

Val Arg Gln Leu Tyr Ile Asp Phe Arg Lys Asp Leu Gly Trp Lys Trp
            20                  25                  30

Ile His Glu Pro Lys Gly Tyr His Ala Asn Phe Cys Leu Gly Pro Cys
        35                  40                  45

Pro Tyr Ile Trp Ser Leu Asp Thr Gln Tyr Ser Lys Val Leu Ala Leu
    50                  55                  60

Tyr Asn Gln His Asn Pro Gly Ala Ser Ala Ala Pro Cys Cys Val Pro
65              70                  75                  80

Gln Ala Leu Glu Pro Leu Pro Ile Val Tyr Tyr Val Gly Arg Lys Pro
            85                  90                  95

Lys Val Glu Gln Leu Ser Asn Met Ile Val Arg Ser Cys Lys Cys Ser
            100                 105                 110

Gly Gly Gly Ser Gly Gly Gly Ser Gly Gly Gly Ser Asp Trp Arg Val
            115                 120                 125

Ile Ile Pro Pro Arg Pro Ser Ala
130                 135
```

FUSION PROTEIN, POLYNUCLEOTIDE, GENETIC CONSTRUCT, PRODUCER, PREPARATION FOR REGENERATION OF CARTILAGE

RELATED APPLICATIONS

This application is a National Phase of PCT Patent Application No. PCT/RU2017/000521 having International filing date of Jul. 13, 2017, which claims the benefit of priority of Eurasian Patent Organization Patent Application No. 201600575 filed on Jul. 14, 2016. The contents of the above applications are all incorporated by reference as if fully set forth herein in their entirety.

FIELD OF THE INVENTION

A group of inventions relates to molecular biology, biotechnology, medicine, veterinary medicine and can be used for the regeneration of cartilage.

BACKGROUND OF THE INVENTION

Cartilage is a type of connective tissue; the cartilage is either a part of a bone that contributes to its mobility, or a separate anatomical structure outside of the skeleton. Articular cartilages, spinal discs, cartilages of ear, nose, pubic symphysis are in direct connection with a bone. Separate anatomical structures constitute a group of cartilages of airways (larynx, trachea, bronchi), of a heart stroma. Cartilages perform integrative-buffer, amortizing, form-supporting functions, participate in the development and growth of bones. Biomechanical functions are carried out through viscoelasticity properties of cartilage.

Diseases and problems associated with the cartilage tissue, can be formally divided into three large groups. The first group includes diseases that may be associated with malformations (e.g., ankylosis, dysplasia) (N. S. Kosinskaya, Developmental disorders of bone and articular apparatus, ed. Medicine, 1966). The second group includes diseases caused by degenerative changes in cartilage during aging and many degenerative processes (e.g. osteoarthritis, degenerative disc disease), metabolic disorders (e.g., osteoporosis, gout, arthrosis, Kashin-Bek disease, ochronosis) and systemic diseases (rheumatism, rheumatoid arthritis, systemic lupus erythematosus, scleroderma, etc.). The third group includes damages of cartilage that arise as a result of physical (mechanical, thermal, etc.), chemical and other traumatic agents (for example, perichondritis, transchondral fracture, damages of cartilage due to microtraumas) (multi-volume manual of surgery, edited by V. V. Petrovsky, V. 5, Moscow—Leningrad, 1960).

The WHO statistics indicates that 80% of the population of working age from 30 to 50 years suffer from various diseases of musculoskeletal system. According to official statistics, tens of millions of people suffer from those or other diseases of cartilage, and there are even more of those who has not sought help from professionals. For example, the number of reported cases of arthritis has almost doubled over the last 20 years, and it seems that this tendency will increase every year. If you interpret the statistics, it turns out that every year 1% of Russians are diagnosed with "arthritis", and about on the same level the number of healthy Americans decreases. The share of only of arthrosis, arthritis and osteoporosis accounts for approximately 3% of the population of Russia or the USA. About 4% of the Earth population suffer from osteoarthritis, and in 10% of cases, osteoarthritis is a cause of disability. According to estimates of various experts, up to 85% of the adult population of Russia face with this disease. In addition, according to the WHO data of 2009 year there were about 20-50 million injuries in the world that led to various problems with the musculoskeletal system or became reasons of disability, and data of 2013 year indicate that each year up to 500 thousand people suffer from spinal cord injuries (spinet.ru/public/dinamika_rasprostraneniy_oda.php). It should also be noted that the treatment of cartilage is a major problem in sports traumatology: cartilage injury causes retirement from sport because it is extremely difficult to achieve its recovery at the moment, with minor damage, and in case of serious damage—it is impossible.

Currently, when damage of cartilage, remedies for pain are most often used—for the treatment of symptomatic pains—non-steroidal anti-inflammatory drugs (NSAIDs), which are used orally or topically in the form of gels (Zupanets I. A., etc. Pharmaceutical care: symptomatic treatment of joint and muscle pain, Pharmacist, 2002, issue 12). However, it is important to restore the structure of the cartilage, the pain syndrome is a secondary phenomenon in injuries. To restore the integrity of the cartilage, drugs—cartilage protectors are currently used, on the basis of chondroitin sulfate and glucosamine. However, it requires a long course, during several months, of every day administration, to improve the condition, and these drugs are only effective for minor lesions of the cartilage. These drugs only stimulate the synthesis of matrix components by existing cells. However, according to the authors view, a number of cells plays a key role in the repair of cartilage. As in the norm, and especially when the damaged cartilage, these cells are present in a small amount, the impact on them to intensify the synthesis of matrix components only insufficiently improves the condition of cartilage.

An invention is known described in U.S. Pat. No. 9,133,259 B2 (Apr. 19, 2012), which refers to protein complexes containing cartilage oligomeric matrix protein (COMP), connected with one or several growth factors (for example, or TGFβ1, or FGF, or both factors) for stimulating chondrogenesis and/or osteogenesis and to restore structures of bones and cartilage. In one embodiment, the growth factor is TGFβ1 or different classes of BMP (bone morphogenetic protein). In the description of the invention it is disclosed that in the most preferred embodiment the protein complex is inside of a biodegradable matrix, which is a plate or bone graft. The matrix further comprises collagen or fibrin. For the therapeutic effect the protein complexes are to be brought into contact with the affected piece of cartilage or bone or implanted into them. However, this is an invasive and time-consuming method having complications.

A fusion protein (variants), including a ligand to MATN1 protein and EGF or TGF or FGF, or IGF protein, is given by the authors of the present invention, the construct components are connected via a flexible link.

MATN1 (matrilin) is a cartilage matrix protein. Mutations in a gene that encodes this protein are associated with various hereditary chondrodysplasias and idiopathic scoliosis (www.ncbi.nlm.nih.gov gene?Db=gene&Cmd=ShowDetailView&TermToSearch=4146, Montanaro L. et al, "*Evidence of a linkage between matrilin-1 gene (MATN1) and idiopathic scoliosis*". Scoliosis 1: 21, 2006).

EGF (Epidermal Growth Factor)—epidermal growth factor, a protein that stimulates cell growth and cell differentiation of the epithelial cover. This protein acts by binding with the receptor of epidermal growth factor on a cell surface, which stimulates the activity of intracellular tyrosine kinases (Dawson J P et al *"Epidermal growth factor receptor dimerization and activation require ligand-induced conformational changes in the dimer interface"*, Mol. Cell. Biol. 25: 17, 2005).

TGF (Transforming growth factor)—transforming growth factor, consisting of two classes of polypeptide growth factors, TGFα and TGF-β. TGFα induces epithelial tissue development. TGF-β is represented by three subtypes—TGFβ1, TGFβ2 and TGFβ3. These proteins play a crucial role in tissue regeneration, cell differentiation, embryonic development. TGF acts by binding with receptors that in turn phosphorylate specific signaling effectors, causing the formation of complexes of signaling proteins. The formed complexes are translocated from the cytoplasm into the nucleus, where they regulate the transcription of specific genes (Matt. P et al, *"Circulating transforming growth factor-{beta} in Marfan syndrome"*. Circulation 120 (6): 526-32, 2005).

FGFs (Fibroblast growth factor)—growth factors of fibroblasts. This family of growth factors is involved in angiogenesis, wound healing and embryonic development. It has been proven that for signal transmission of growth factors of fibroblasts interaction with proteoglycans located on the cell surface is necessary. Growth factors of fibroblasts play a key role in the processes of proliferation and differentiation of wide spectrum of cells and tissues (embryology.med.unsw.edu.au/embryology/index.php/Developmental_Signals_-_Fibroblast_Growth_Factor; dic.academic.ru/dic.nsf/ruwiki/188282).

IGF—human Insulin-like growth factor of the first type (IGF-1), a peptide growth factor mediating the growth promoting effects of growth hormone (GH), is represented by a polypeptide consisting of 153 amino acids, with a molecular weight of about 7 kDa. Under the influence of GH, IGF-1 is produced in the liver and other tissues. IGF-1 stimulates the proliferation of cells of most tissues, especially of bone, cartilage and muscle. IGF-1 is an anabolic agent for which an improved metabolism has been demonstrated (Meyer N. A. et al. 1996. J. Trauma 31 (6): 1008-1012) after various types of damage. Treatment by IGF-1 enhances tissue healing (Martin, P. 1997. Science 276: 75-81. 1997; Steenfos H. 1994. Scand J Plast Reconstr Hand Surg 28: 95-105; Pierre et al. 1997. J Bum Care Rehab 18 (4): 287-291).

A fusion protein proposed by the authors of the present invention is tropic to the matrix of the cartilage, due to the fact that it contains a ligand to the protein of cartilage matrix MATN1 (matrilin), respectively, it may be introduced both parenterally and systemically, which facilitates its application. This protein also contains a growth factor of EGF or TGF or FGF, or IGF. Components of the fusion protein are connected via a flexible link, which allows to achieve the functioning of each component of the protein.

The technical result from the use of a fusion protein, or a drug based on it according to the invention (variants) is expressed in the simplification of the treatment of cartilage injuries. This is achieved due to the absence of a mandatory need for the introduction of the protein or of the drug locally, thanks to the targeted delivery due to the use of an element in a structure of the fusion protein that binds exclusively with the protein of cartilage, being the one proposed by the authors. Also this technical result is achieved by local introduction due to the more simple form of administration, by injection, without the use of a matrix of a special composition, which is to be designed provisionally.

The technical result from the use of the fusion protein, or the drug based on it according to the invention (variants) is expressed in safety increase and complications decrease from therapy of cartilage injuries, due to the use of more secure means of delivery of the fusion protein to the cartilage.

The technical result from the use of the fusion protein, or the drug based on it according to the invention (variants) is expressed in an increase of efficiency of treatment of lesions of cartilage due to a more uniform distribution of the fusion protein in the cartilage, due to the affinity to the matrix protein, in contrast, for prototype, to a clearly defined introduction place when introduction in the composition of the matrix, or even by injection.

The technical result from the use of the fusion protein, or the drug based on it according to the invention (variants) is also to expand the range of active substances or preparations, respectively, to restore the structure of cartilage. When contraindications to the use of analogues or unwillingness to use analogs because of their above described drawbacks, the protein or drug that has a different principle of operation will allow for the regeneration of cartilage. Due to the fact that the problem of regeneration of cartilage is very serious, and the launch of a drug is not achieved by majority, the proposed invention allows to increase the odds in the fight against this widespread disease.

The authors of the present invention also propose a genetic construct (variants) for expression of the fusion gene in producer cells, or target organism (variants), encoding a fusion protein (variants), including the ligand to MATN1 protein and EGF or TGF or FGF, or IGF, connected via a flexible link. A drug is proposed based on at least 1 of such construct, for parenteral administration. This construct and preparation on its basis are not known from the prior art. The advantages and the technical result of the mentioned genetic construct and preparation on its basis are the same as a of a fusion protein, however, there are additional benefits.

Thus, the technical result is in an increase of the duration of the effect and is achieved by the use of the genetic construct, from which a fusion protein is synthesized after the introduction into the body; and by the fact that this genetic construct contains elements that lead to mRNA stability and, consequently, increase the half-life time of mRNA, as a result the protein synthesis from one mRNA molecule is performed more number of times, and as a result the amount of protein synthesized increases; and also by the fact that the nucleotide sequence of the fusion gene is codon-optimized for expression in a target organism, as a result, the protein synthesis is more intensive. When implemented in practice this will significantly reduce the amount of the input plasmid DNA (in 10-50 times) in comparison with the doses currently used in domestic and world practice in gene therapy.

In addition, the technical result is to increase security. This technical result is achieved in that a protein synthesized in the body from the genetic construct is exposed to the natural posttranslational processing, and a proper folding of the protein is provided due to cellular chaperones. This technical result is achieved also due to the presence of regulatory sequences, like a silencer and/or an insulator, in the design of such genetic construct, in one embodiment of the invention, which also helps to control the amount of the protein synthesized, and, in principle, the protein synthesis as such, and, accordingly, the action of the drug: if necessary it is possible in a quick period of time to stop or reduce gene expression. In the latter case, implementation of tissue-specific expression is possible when needed.

The technical result is also in the simplification and cheapening of production of the regeneration drug by avoidance of the production and purification of protein preparations in vitro, due to the fact that the protein synthesis occurs in vivo. Production, purification and storage of DNA preparations is economically more profitable than of protein ones, since the former are more stable, they can be produced in large quantities at lower costs.

Obtaining of medicines to restore cartilage structures that would be convenient for the administration is an important task of modern medicine and veterinary medicine. Oral way of administration of medicines is the most simple, safe and is the most widespread. Preferably, this method is used for prescription of medications that are well-absorbed by the mucous membrane of stomach or intestine. Therapeutic drug level in the blood is achieved after 30-90 min after its administration and persists for 4-6 hours, depending on the properties of the active ingredient and the composition of the drug. The advantages of this method of introduction include the possibility of introduction of different dosage forms (powders, tablets, pills, coated tablets, decoctions, mixtures, etc.), the simplicity and accessibility of the method; the method does not require the observance of sterility. The disadvantages of oral administration of medicines should include more slow development of therapeutic effect than with other methods of drug intake; rate and bioavailability are individual for each patient, as they are influenced on by food, organic and functional condition of the gastrointestinal tract, intake of other medications; oral administration is ineffective for drugs poorly absorbed or decaying in the digestive tract; also, oral administration is difficult or impossible if vomiting and if a patient is in an unconscious condition (sestrinskoe-delo.ru/puti-i-sposobi-primeneniya-lekarstvennich-sredstv).

From the document WO2013059885A2 (May 2, 2013) polypeptide constructs are known that contain a peptide or polypeptide signaling ligand that is bound with an antibody or its antigen-binding part. The half-life time of the antibody in serum and bioespeleo may be modified based on the modification of the interaction between the antibody and the neonatal Fc receptor (FcRn). The document does not provide information about the possibility of oral administration of such structures.

In documents RU 2562232 C2 (Nov. 3, 2009) and RU 2489423 (Feb. 2, 2007) analogs of the DNA-alkylating drug SS-1065 and their conjugates are given for the selective delivery and/or controlled release of one or several DNA-alkylating drugs. These types of conjugates the inventors propose to use for the treatment of diseases caused by undesirable cell proliferation (neoplastic disease). Conjugates may include various proteins, e.g., transferrin, or epidermal growth factors (EGF), or interleukins (IL-2, IL-6), or transforming growth factors (TGF) such as TGF-α and TGF-β, or others. Also, a part of the conjugate is an antibody having modifications in amino acid residues that interact with Fc-receptors. The elements of the conjugate are linked by a linker, for example, that includes a triazole group, a single bond (—C(O)—, —O—, —S—) can also be a linker. Preferably, the linker has a small size (linker, which has not more than 4 connecting atoms). Pharmaceutical compositions containing the conjugates are proposed by the inventors to be introduced by a variety of ways (oral administration, topical application or by injection). However, a non-specific delivery of the conjugate and its penetration into non-target cells is possible.

From the document U.S. Pat. No. 8,932,589 (B2) (Mar. 12, 2013) compositions are known containing a fusion protein that includes a Klotho protein or an active fragment thereof, FGF or a fragment thereof and possibly a modified Fc-fragment, which increases the affinity or the half-life in serum. The Klotho protein or its active fragment is able to bind with a receptor of FGF. Components of a fusion protein may be connected by a peptide bond or through a linker. Compositions are used to treat metabolic disorders and age-related diseases (including diseases such as osteoporosis and osteoarthritis). Compositions are presented in solid, liquid form or in the form of an aerosol, the compositions can be administered in a number of ways, including oral, but the most preferred one is the intravenous one—drip or bolus injection. It is desirable to be noted that the Klotho protein is not specific for cartilage tissue.

A fusion protein proposed by the authors of the present invention is tropic to the matrix of the cartilage, due to the fact that contains the ligand to MATN1 protein of the cartilage matrix. This protein also contains a growth factor of EGF or TGF or FGF, or IGF, as well as the Fc-fragment of an antibody or a polypeptide which binds with FcRn, for parenteral or oral delivery. Components of the fusion protein are connected via flexible links, which allows to achieve the operation of each component of the protein.

The technical result from the use of a fusion protein, or a drug based on it according to the invention (variants) is in an increase of efficiency of treatment of lesions of the cartilage as the fusion protein works only in cartilaginous tissue. This is achieved due to the impact of the fusion protein or of the drug on its basis exclusively on the cartilage tissue, due to the use of the ligand to matrilin proposed by the authors.

The technical result from the use of the fusion protein, or the drug based on it according to the invention (variants) is in increasing safety by reducing complications, the absence of unexpected results from the treatment of cartilage injuries due to the impact of a fusion protein, or drug, exclusively on the cartilage tissue, due to the use of the ligand to matrilin proposed by the authors.

The technical result from the use of the fusion protein, or the drug based on it according to the invention (variants) is also to expand the range of active substances or preparations, respectively, to restore the structure of cartilage.

In documents US 2011092677 (A1) (Apr. 21, 2011) and WO2004020404 (A2) (Mar. 11, 2004) a trans-body is described containing one or more variable domain or CDR of antibodies to one or more different antigens for the treatment or prevention of disease, and transferrin or modified transferrin, which can treat also some forms of arthritis, when TNFa is used as antigen(s). TGF or EGF or FGF may be antigen(s), then the application will be different, but it is not specified in the document. Other antigens mentioned in the document are targets for blocking by trans-bodies. Preferably, these modified groups of transferrin do not undergo glycosylation or practically do not undergo glycosylation, do not bind iron and/or transferrin receptor, which positively affects the duration of half-life. Also, compositions are proposed containing the mentioned above trans-bodies. The compositions are administered in different ways, parenterally or orally. These trans-bodies for the treatment of arthritis act through binding and, consequently, blocking TNFa, and trans-bodies are not targeted to any tissue. Thus, they do not cause the regeneration of a cartilage tissue. Trans-bodies binding with the specified growth factor(s) are intended to block the target. In the case of the present invention proposed by the authors the methodology of use of a growth factor is different.

A fusion protein proposed by the authors of the present invention is tropic to the matrix of the cartilage, due to the fact that contains the ligand to MATN1 protein of cartilage matrix. This protein also contains a growth factor of EGF or TGF or FGF, or IGF, as well as transferrin or its fragment, for parenteral or oral delivery. Components of the fusion protein are connected via flexible links, which allows to achieve the operation of each component of the protein.

The technical result from the use of a fusion protein, or a drug based on it according to the invention (variants) is in the regeneration of cartilage through targeting of the fusion protein to the matrix of cartilage, as well as to attract and stimulate growth of the desired cells through the use of a growth factor in the construct of fusion protein.

The technical result from the use of the fusion protein, or the drug based on it according to the invention (variants) is in increasing the safety by reducing complications, by the absence of unexpected results from the treatment of cartilage injuries due to the action of a fusion protein, or the drug, exclusively in the cartilage tissue, due to the use of the ligand to matrilin proposed by the authors.

The technical result from the use of the fusion protein, or the drug based on it according to the invention (variants) is also to expand the range of active substances or preparations, respectively, for the treatment of cartilage injuries, which can be administered orally.

The invention described in U.S. Pat. No. 9,133,259 B2 (Apr. 19, 2012), which refers to protein complexes containing cartilage oligomeric matrix protein (COMP), connected with one or more growth factors, for example, TGFβ1, or FGF, or both factors, for stimulating chondrogenesis and/or osteogenesis and restoration of structures of bones and cartilage. However, unlike the claimed invention, this application doesn't offer oral administration of drugs containing the above mentioned protein complexes. So, in the description of the invention it is disclosed that in the most preferred embodiment the protein complex is inside of a biodegradable matrix, which is a plate or bone graft. The matrix further comprises collagen or fibrin. For the therapeutic effect the protein complexes need to be brought into contact with the affected piece of cartilage or bone or implanted in them, which is an invasive and time-consuming method having complications.

In document WO 2004/062602 A2 (Jul. 29, 2004) compositions and methods for the targeted delivery of substances in polarized cells (intestinal epithelium) are proposed for therapeutic, prophylactic or diagnostic purposes. Compositions contain the design of several elements: an element of binding with the surface of a polarized cell; an element for penetration of the composition into the cell; an element, a polypeptide or a chemical group, which, in fact, is used for therapeutic, prophylactic or diagnostic purposes. For example, if the composition is used for diagnostic purposes, the third element can be a contrast agent, for therapeutic purposes—antibody or a fragment thereof. The first two elements can constitute a polypeptide, an antibody or a fragment of an antibody, which can bind, for example, with a transferrin receptor or FcRn. Design elements are covalently or non-covalently linked with each other. Compositions are for oral administration. However, nothing is said about additional elements allowing for the targeted delivery of molecules which have passed through the epithelium layer. The text describes only the delivery of molecules through the epithelial layer, the further path of the input molecules is not disclosed. Respectively, the used third element of the design mediates that the construct remains within the epithelial cell or spreads through the body and produces systemic effects.

The idea of creating constructs or fusion proteins which include or bind with transferrin or a modified transferrin, and include the Fc-fragment of an antibody or a group binding with FcRn, i.e. such constructs or fusion proteins include both transferrin and the Fc-fragment, for different purposes, for example, to improve the properties of existing proteins, for the creation of transport proteins, for obtaining highly efficient therapeutic agents, etc., is considered in the documents U.S. Pat. No. 8,173,860 B2 (May 8, 2012), WO 2001/046254 A1 (Jun. 28, 2011), WO 2012/116453 A1 (Sep. 7, 2012), WO 2015/070014 A1 (May 14, 2015), WO 2012/170969 A2 (Dec. 13, 2012). For all of them, except the described in the first document, oral administration is provided. Such structures are preferably administered parenterally. Preparations for the regeneration of cartilage are not given.

In documents RU 2555532 C2 (Nov. 6, 2009) and RU 2490278 C2 (Dec. 19, 2008) different variants of antibodies are presented specific against IL-1R1, which is expressed on various cell types, or of α-receptor of human interleukin-4 (hIL-4Rα). The claimed antibodies can be used for treatment of disorders mediated by IL-1R1 including rheumatoid arthritis, but the key diseases that the authors propose to treat with these antibodies are asthma and COPD (chronic obstructive pulmonary disease). These antibodies contain the frame and one or more variable loops, in which the amino acid sequence of the loop or loops is mutated to create an antigen-binding site that binds with the antigen target. Such designs include transferrin, and the binding phase contains a variant of Fc region with increased binding with Fc-receptor FcRn to increase the half-life in serum. Compositions containing these constructs are introduced in a variety of ways, including orally—in a pill or powder, but pre-emptive is the parenteral route of administration. That invention allows to slow the disease, as the antibodies block a molecule that mediates the development of rheumatoid arthritis. However, it is not able to cause regeneration of cartilage in the required amount, due to the fact that does not affect the number of cells synthesizing the substance matrix.

From the document U.S. Pat. No. 8,932,589 (B2) (Mar. 12, 2013) compositions are known containing a fusion protein that includes Klotho protein or a fragment thereof, FGF or a fragment thereof and possibly a modified Fc-fragment, which increases the affinity or the half-life in serum. Klotho protein or its active fragment is able to bind with a receptor of FGF. Components of the fusion protein can be connected by a peptide bond or through a linker. Compositions are used to treat metabolic disorders and age-related diseases, including diseases such as osteoporosis and osteoarthritis. Compositions are presented in a solid, liquid form or in the form of an aerosol, the compositions can be administered in a number of ways, including orally, but the most preferred way is the intravenous administration—drip or bolus injection. It should be noted that Klotho protein is not specific to cartilage tissue, respectively treatment with the use of this fusion protein is not a targeted one.

A fusion protein proposed by the authors of the present invention is tropic to the matrix of the cartilage, due to the fact that contains the ligand to MATN1 protein of the cartilage matrix. This protein also contains a growth factor of EGF or TGF or FGF, or IGF, as well as transferrin or its fragment, as well as the Fc-fragment of an antibody or a polypeptide which binds with FcRn, for parenteral or oral delivery. Components of the fusion protein are connected via flexible links, which allows to achieve the operation of each component of the protein.

The technical result from the use of a fusion protein, or a drug based on it according to the invention (variants) is in the increased efficacy of regeneration of cartilage through targeting of the fusion protein to the matrix of cartilage. Thus, the drug accumulates in the target tissue—is present there in a high concentration, unlike a drug just circulating in the bloodstream. Also, in one embodiment, other growth factors are used—EGF or TGF or IGF.

The technical result from the use of the fusion protein, or the drug based on it according to the invention (variants) is in increasing the safety due to the targetnode of its impact, which eliminates unexpected reactions and side effects in the body.

The technical result from the use of the fusion protein, or the drug based on it according to the invention (variants) is also to expand the range of active substances or preparations, respectively, for the treatment of cartilage injuries, which can be administered parenterally or orally.

Parenteral administration of the described above fusion protein(s), containing the transport domain (transferrin/transferrin fragment and/or Fc-fragment of an antibody/polypeptide binding with FcRn), is given also by the authors of the present invention together with fusion protein(s) that do not contain a transport domain, also as part of the preparation, for the regeneration of cartilage, in one embodiment. In this case, the technical result coincides with that from the use of such active substances. Such proteins also longer persist in the body.

The technical result from the use of a drug on the basis of 2 fusion proteins that do not contain transport domain is the same as from the use of such active substances.

The authors of the present invention also proposed a genetic construct (variants) for expression in the cells of a target organism (variants) encoding a fusion protein (variants), including a ligand to MATN1 protein, a growth factor of EGF or TGF or FGF, or IGF, Fc-fragment of an antibody or a polypeptide binding with FcRn and/or transferrin or a fragment thereof, the components are connected via flexible links. The authors suggest injecting this genetic construct, at least 1 item in the formulation, in one embodiment together with the genetic construct described above not containing the transport domain, at least 1 item in the formulation. This construct and preparation on its basis, including the addition of the specified above additional component(s) are not known from the prior art. The advantages and the technical result are the same as of fusion proteins described above coded by it, as well as of the genetic construct described above not containing the transport domain, and the drug based on it.

Thus, drugs based on fusion protein(s) targetnode to cartilage tissue, for the treatment of diseases of the cartilage due to induction of cartilage regeneration, being administered both parenterally and orally, are is not currently known. Also drugs based on genetic construct(s) from which in the cells of the target organism such fusion protein(s) is(are) synthesized, which are administered parenterally, are not known.

Accordingly, inventions used to obtain the above mentioned fusion proteins are not known: polynucleotides, genetic constructs, producers; genetic structures: polynucleotides, producers. The technical result from them is to obtain proteins, genetic constructs, respectively, and the preparations according to the invention.

Subject Matter

An urgent task of the present time is the development of drugs that would have resulted in a significant regeneration of a damaged cartilage, wherein they would act targeted and be easy to use, and also safe and economical in production and use. This problem is solved by the proposed group of inventions (options).

A group of inventions (variants) is proposed: (1) a fusion protein comprising a ligand to MATN1 protein, characterized by the amino acid sequence SEQ ID NO:1, and a growth factor of EGF, TGF, FGF, IGF, characterized by the amino acid sequence of SEQ ID NO:2, 3, 4 or 5, respectively, the components of the structure are connected via a flexible link, characterized by the amino acid sequence SEQ ID NO:6; (2) the fusion protein (1), further containing the Fc-fragment of an antibody, characterized by the amino acid sequence SEQ ID NO:7 or a polypeptide binding with FcRn, characterized by the amino acid sequence SEQ ID NO:8, and/or transferrin, characterized by the amino acid sequence SEQ ID NO:9 or its fragment characterized by the amino acid sequence SEQ ID NO:10, construct components are connected via a flexible link characterized by the amino acid sequence SEQ ID NO:6; (3) a polynucleotide encoding the fusion protein (1) or (2) codon optimized for expression in the producer cells or a target organism, (4) a genetic construct for synthesis in cells of the producer, or a target organism of the fusion protein (1) or (2), including the polynucleotide (3) and other elements, allowing to realize the identified purpose, (5) a producer of the fusion protein (1) or (2), (6) a producer of the genetic construct (4) based on bacterial cells, a drug for the regeneration of cartilage containing at least one (7) fusion protein (1) or (2) or (8) genetic construct for its/their synthesis in cells of the target organism as an active agent in an effective amount and a physiologically acceptable carrier and a buffer solution, for parenteral or (9) in the case of a drug based on at least one fusion protein (2), —oral administration, in the latter case the drug is enclosed in enteric coating.

DETAILED DESCRIPTION OF THE INVENTION

The proposed group of inventions: a fusion protein, a polynucleotide, a genetic construct, a producer, a drug for regeneration of cartilage (variants).

Fusion proteins are proposed, each includes a ligand to MATN1 protein and a growth factor of EGF, TGF, FGF, IGF, construct components are connected via a flexible link, the sequences of components are shown in the Sequence listing. Also fusion proteins are given which additionally contain at least one component of Fc-fragment of an antibody, a polypeptide binding with FcRn, transferrin, or a fragment thereof, the construct components are connected via a flexible link, the sequence of components is shown in the Sequence listing.

Polynucleotides are given encoding the described fusion proteins, codon-optimized for expression in the cells of a producer or a target organism. A target organism is the organism which requires the repair of cartilage. When the amino acid sequence of the protein is known, the skilled in the art can obtain the nucleotide sequence. Codon optimization is carried out independently, using information about the frequency of occurrence of codons in the producer, for example, in a database [e.g., Nakamura Y, Gojobori T, Ikemura T. Codon usage tabulated from international DNA sequence databases: status for the year 2000. Nucleic Acids Res. 2000 Jan. 1; 28(1):292], either using specialized software such as represented on the website www.encorbio.com/protocols/Codon.htm or molbiol.ru/scripts/01_19.html.

Genetic constructs for expression of the described polynucleotides in the cells of a producer or a target organism are proposed; each construct includes, in addition to a polynucleotide, elements allowing to realize the specified destination.

The genetic construct for expression in the cells of the target organism means a "short" linear design, or a recombinant vector, in a circular or linear form, which can be represented by a plasmid or viral vector.

The genetic construct for the synthesis of a fusion protein in cells of a producer must contain, in addition to the fusion gene encoding the protein according to the invention, elements for the maintenance and amplification, mostly in large quantities, and effective functioning according to the purpose, and also for selection of a transformant.

The genetic construct for synthesis of fusion protein in the cells of the target organism, the recombinant vector should contain, in addition to the fusion gene encoding the protein according to the invention, elements for the maintenance and amplification and efficient operation in accordance with intention.

Such genetic constructs are economically most profitable to be accumulated in prokaryotic cells, mainly bacterial cells. In this regard, such genetic constructs of the present invention contain elements for maintenance and amplification, mainly in large quantities, in bacterial cells. These material elements are a prokaryotic origin of replication for maintenance in a cell with a medium, preferably a high number of copies per cell, and a reporter gene for possibility of selection of the producer strain—a gene causing resistance to an antibiotic, or a gene finalizing auxotrophy. A suitable origin of replication for, for example, a plasmid vector, is represented, for example, by pM1 (der.), ColE1 (der.) and F1, F1 and pUC, SV40, but is not limited to them. Also an element for integration into the genome of the producer may be contained. For example, 3' AOX1 or 18S rRNA for yeast.

Under the elements for selection of a transformant, as a rule, a gene causing resistance to an antibiotic, or a gene finalizing auxotrophy are meant. When using bacteria as a producer the selective marker may be represented, for example, by the gene of resistance to ampicillin or kanamycin, or tetracycline; yeast—for example, the gene LEU2 or TRP1, or URA3; fungi—for example, the gene of resistance to bialaphos or hygromycin or aureobasidin or bleomycin; plants—for example, the gene of resistance to kanamycin or bialaphos; mammalian cells—for example, the gene of resistance to neomycin.

A genetic construct for synthesis of a fusion protein in the cells of the target organism, a "short" linear construct, should contain, in addition to the fusion gene encoding the protein according to the invention, the elements for the effective functioning according to specification. Production of such a genetic construct is mostly economically advantageous to be carried out using the polymerase chain reaction (PCR).

Under the elements for effective functioning, for expression of the encoded protein, signals for transcription, a promoter, signals of initiation of translation, the start codon and the stop codon(s), transcription termination sequences, regulatory sequences are meant. The presence of a secretory sequence is also possible.

When organism *Escherichia coli* is used as a producer, promoter can be represented, for example, by the promoter of the lactose operon, tryptophan operon; yeast—for example, promoter of the gene of acid phosphatase, alcohol dehydrogenase gene, the gene of glyceraldehyde-3-phosphate dehydrogenase, the gene of the galactose metabolism; fungi—for example, promoter of the gene of cellobiohydrolase, either α-amylase or glucoamylase, or glyceraldehyde-3-phosphate dehydrogenase, or the gene abp1; plants—for example, CaMV 19S RNA promoter or the CaMV 35S RNA promoter or a gene nepalisite promoter. When cells of a mammal are used as the producer, for example, a promoter can be represented by a natural promoter with its regulatory elements (e.g., CaM kinase II, CMV, nestin, L7, BDNF, NF, MBP, NSE, p-globin, GFAP, GAP43, tyrosine hydroxylase, subunit 1 of kainate receptor and subunit B of the glutamate receptor, and others) or by a synthetic one with regulatory sequences, to obtain the desired expression pattern (ratio of expression length and level) of the target gene at the transcriptional level.

Signals of the initiation of translation is the sequence of Shine—Dalgarno [Kapp L. D., Lorsch J. R. The molecular mechanics of eukaryotic translation/Annual Review of Biochemistry 73/2004, 657-704] in prokaryotes and the Kozak sequence in eukaryotes [Kozak M. (1986) "Point mutations define a sequence flanking the AUG initiator codon that modulates translation by eukaryotic ribosomes", Cell 44, 283-292]. When using mammalian cells, the Kozak sequence directly before the start codon ATG can increase the expression [Kozak M. Recognition of AUG and alternative initiator codons is augmented by G in position +4 but is not generally affected by the nucleotides in positions +5 and +6. EMBO J. 1997; 16(9):2482-2492].

Terminating sequence is one of the elements determining mRNA stability. Termination sequence for eukaryota contains consequently a stop codon, the 3' noncoding region with polyadenylation signal and site, stop codon, thereby the stability of mRNA is maintained, and the proper termination of transcription and export of mRNA from the nucleus are performed. The terminating sequence is a native one, i.e. original for cDNA of a protein used or other, stronger, which is represented, for example, for mammalian cells, by the termination sequence of bovine growth hormone (BGH), but it is not limited, and may contain an additional stop codon before the 3' noncoding region. An example of a terminating sequence for the plant cells is such of nopalin synthase gene (NOS T).

Regulatory sequences are nucleotide sequences that can affect the gene expression at the level of transcription and/or translation, as well as on the mechanisms that ensure the existence and maintenance of functioning of a genetic construct. Possible regulatory sequences relative to the promoter are an enhancer to increase the expression level via improved interaction between RNA polymerase and DNA, insulator to modulate the functions of enhancer, silencer, or fragments thereof, to decrease the level of transcription, for example, for tissue-specific expression, the 5' noncoding region up to the promoter, including intron. When a silencer or insulator is used as part of the design, it is possible to regulate the expression of a target gene.

Genetic construct for the protein synthesis in eukaryotic cells in one embodiment according to the present invention contains one of the above-mentioned regulatory sequences, depending on a variant of the genetic construct based on the choice of promoter and on the desired parameters of expression of the target gene. Other regulatory sequences:
  noncoding region downstream from the promoter, including intron, to increase the stability of mRNA and increase the expression of the target gene.

Genetic construct for protein synthesis in eukaryotic cells according to the present invention in one embodiment further comprises such a regulatory element.

For secretion of the fusion proteins according to the invention, at the N-end of a polynucleotide encoding the target gene a signal peptide suitable for the used producer or a target organism is placed. Examples of such secretory sequences are described in the literature [for example, for *E. coli* in the patent of Russian Federation No. 22198179, priority date 15 Sep. 1999 for yeast—in the patent of Russian Federation No. 2143495, priority date 8 Jul. 1994, U.S. Pat. No. 4,546,082, the priority date of 17 Jun. 1982, the European patent No. 2116201, 123294, 123544, 163529, 123289, the application for the invention of Denmark 3614/83, the priority date of 8 Aug. 1983 for plants—in articles Kapila J, Rycke R D, Van Montagu M, Agenon G (1997) An *Agrobacterium*-mediated transient gene expression system for intact leaves. Plant Sci 122: 101-108, Stiefel, V., Ruiz-Avila, L., Raz, R., Valles, M. P., Ghez, J., Pages, M., Martinez-lzquierdo, J. A., Ludevid, M. D., Langdale, J. A., Nelson, T., and Puigdoménech, P. (1990). Expression of a maize cell wall hydroxyproline-rich glycoprotein gene in early leaf and root vascular differentiation. Plant Cell 2, 785-793].

Moreover, a native or heterologous secretory sequence may be contained, codon-optimized for a cell in which the synthesis of a fusion protein according to the invention is performed. In one embodiment of the invention, genetic construct for the synthesis of a fusion protein in mammalian cells includes the secretory sequence TPA (tissue-type plasminogen activator isoform 1 preproprotein [*Homo sapiens*], NCBI Reference Sequence: NP_000921.1). The advantage of using TPA secretory sequence is in extensive previous clinical experience, and also in that it demonstrates a high performance in relation to the expression of the secreted protein from a variety of target genes.

Additional elements required for the functioning of an expression system may also be contained. Based on the existing level of technology and the known and obvious variants of such elements and their use, genetic construct according to the present invention may contain any combinations meeting the above-mentioned criteria, using which expression of a fusion gene is performed in producer cells or a target organism.

The sequence in which the elements described are positioned in the genetic construct is understandable to an expert in this field.

A genetic construct for expression in the producer cells can be represented, depending on compatibility with the producer, by a viral, plasmid, fosmid, cosmid or any other possible vector. For example, if *E. coli* cells are selected as a producer, the gene can be a part of a bacteriophage, for example, on the basis of phage λ, or plasmids, for example, on the basis of the pBR or pUC, and the like. When *Bacillus subtilis* is used as a producer organism, the gene can be, for example, in a plasmid based on pUB. When yeast are used as a producer, a genetic structure can be represented, for example, by a plasmid-based YEp or YRp or YCp or YIp. When mammalian cells are used as a producer, the genetic construct can be represented, for example, by a plasmid, for example, pVAX1, pcDNA3.1, or AAV, but is not limited to them.

Suitable genetic constructs for expression in the cells of the target organism—mammals—are represented by well-known to the average skilled in the art and described in the literature [Hartikka J, Sawdey M, Cornefert-Jensen F, Margalith M, Barnhart K, Nolasco M, Vahlsing H L, Meek J, Marquet M, Hobart P, Norman J, Manthorpe M. An improved plasmid DNA expression vector for direct injection into skeletal muscle. Hum Gene Ther. 1996 Jun. 20; 7(10):1205-17 etc.], as well as by those that can be created by an average person skilled in the art using the guidelines on the elements of the vectors ["Cloning Vectors", ed. Pouwls et al., Elsevier, Amsterdam—New York-Oxford, 1985, ISBN 0 444 904018, Williams J A, Carnes A E, Hodgson C P. Plasmid DNA vaccine vector design: impact on efficacy, safety and upstream production. Biotechnol Adv. 2009 July-August; 27 (4): 353-70. doi: 10.1016/j.biotechadv.2009.02.003. Epub 2009 Feb. 20. Review H Ap.].

Preferred genetic constructs for use in humans are vectors tested on humans, containing the above-described elements with the corresponding regulatory sequences, possibly modified to match the stated criteria, which allows to reduce the number of required studies for registration of a drug. However, the use of other genetic structures is possible that contain the required elements described.

Producers of fusion proteins described are given, based on a prokaryotic or an eukaryotic organism. A prokaryotic producer is represented, for example, by *Escherichia coli*, *Bacillus subtilis*, eukaryotic producer—fungi, cells of plants, mammals.

The above examples are given to illustrate the implementation of inventions (genetic construct, producer), but the implementation is not limited to such. To date in the scientific literature (for example, textbooks on molecular biology, biotechnology, articles, for example, available at www.labome.ru/method/Recombinant-Protein-Expression-Vector-Host-Systems.html, specialized websites in internet with databases, for example, of vectors) a great number of expression systems and methods of their creating and working with them is described, in connection with which for an expert it is clear that the given description of the group of inventions allows to implement them.

Variants of the preparation for regeneration of cartilage are proposed. Each variant for parenteral administration contains at least one of the described fusion proteins, as the active agent, or at least one of the described genetic constructs of one species for the synthesis of the fusion protein in the cells of the target organism, in an effective amount, and a physiologically acceptable carrier and a buffer solution. In the preparation each fusion protein is only of two components, or, if domain(s) for oral administration is(are) used, only of three and/or four, genetic construct—encodes one fusion protein (2 to 4 components). Each variant for oral administration contains 1 fusion protein of 3 or 4 components in an effective amount and a physiologically acceptable carrier and a buffer solution. Pharmaceutically acceptable carriers and buffer solutions are known from the art and include those described in various texts, such as Remington's Pharmaceutical Sciences. As a consumer of the drug a person or animal, including pets or farm animals, may perform. The oral form of the drug is administered as part of a special capsule, which dissolves in the intestine and partially the stomach, in enterosolubiles coverage. For example, liposomes may be used as in the oral recombinant drug Reaferonum-Lipint. Fillers of capsules also may be contained, which additionally sparing reduce the acidity (carbonates) and protect the protein. Interaction with the receptor occurs rapidly, and the protein does not have time to destroy.

The authors of this invention have conducted laboratory tests confirming the possibility of implementation of the described inventions and their effectiveness. The results obtained are illustrated by the following examples.

Example 1. Modeling of Fusion Proteins

For the modeling of proteins the following steps were carried out:
1. Search of components of the fusion protein
2. Build of a model of the whole protein to determine the orientation of domains
3. Build of models for each domain (using samples of the 3D structures and ab initio)
4. Docking of models using models of the whole protein.

To obtain the most realistic results in an automated regime the algorithm I-Tasser was used for modeling the proteins.

Simulated fusion proteins represented by a combination of components SEQ ID NO:1, SEQ ID NO:2/3/4/5, as well as those additionally containing component(s) SEQ ID NO 7/8 and/or SEQ ID NO 9/10, components in all proteins connected via SEQ ID NO 6 flexible link, were analyzed using the ProtParam program (au.expasy.org/tools/protparam.html), on amino acid sequences of these proteins. The following data were obtained.

Simulated fusion proteins are represented by a combination of components SEQ ID NO:1, 2, linked via SEQ ID NO:6, consist of 77 aa, SEQ ID NO:1, 3 linked via SEQ ID NO:6-136 aa, SEQ ID NO:1, 4, linked via SEQ ID NO:6-147 aa, SEQ ID NO:1, 5, linked via SEQ ID NO:6, consist of 177 aa, and have a molecular weight 8.4 kDa, pI 5.1, 15 kDa, pI 8.74, 16.3 kDa, pI 9.81, 19.2 kDa, pI 9.46, respectively.

Simulated fusion proteins are represented by a combination of components SEQ ID NO:1, 2, 7, linked via SEQ ID NO:6, consist of 316 aa, SEQ ID NO:1, 3, 7, linked via SEQ ID NO:6, —375 aa, SEQ ID NO:1, 4, 7, linked via SEQ ID NO:6-386 aa, SEQ ID NO:1, 5, 7, linked via SEQ ID NO:6, consist of 416 aa, and have a molecular weight 34.7 kDa, pI 6.34, 41.3 kDa, pI 8.4, 42.7 kDa, pI 9.1, 45.5 kDa, pI 8.94, respectively. When SEQ ID NO:9 component is added with the use of SEQ ID NO:6, proteins increase by 709 aa, the molecular mass—by 77.7 kDa. When SEQ ID NO:10 component is added with the use of SEQ ID NO:6 instead of using SEQ ID NO:9 component with the use of SEQ ID NO:6, proteins increase by 27 aa, molecular mass—by 2.4 kDa.

Simulated fusion proteins are represented by a combination of components SEQ ID NO:1, 2, 8, linked via SEQ ID NO:6, consist of 126 aa, SEQ ID NO:1, 3, 8, linked via SEQ ID NO:6—185 aa, SEQ ID NO:1, 4, 8, linked via SEQ ID NO:6-196 aa, SEQ ID NO:1, 5, 8, linked via SEQ ID NO:6, consist of 226 aa, and have a molecular weight 13.3 kDa, pI 5.3; 19.9 kDa, pI 8.7, 21.2 kDa, pI 9.65, 24.1 kDa, pI 9.35, respectively. When SEQ ID NO:9 component is added with the use of SEQ ID NO:6, proteins increase by 709 aa, the molecular mass—by 77.7 kDa. When 10 component is added with the use of SEQ ID NO:6 instead of using SEQ ID NO:9 component with the use of SEQ ID NO:6, proteins increase by 27 aa, molecular mass—by 2.4 kDa.

Simulated fusion proteins are represented by a combination of components SEQ ID NO:1, 2, 9, linked via SEQ ID NO:6, consist of 786 aa, SEQ ID NO:1, 3, 9, linked via SEQ ID NO:6—845 aa, SEQ ID NO:1, 4, 9, linked via SEQ ID NO:6-856 aa, SEQ ID NO:1, 5, 9, linked via SEQ ID NO:6, consist of 886 aa, and have a molecular weight 86.1 kDa, pI 6.52, 92.6 kDa, pI 7.70, 94 kDa, pI 8.3, 96.9 kDa, pI 8.25, respectively.

Simulated fusion proteins are represented by a combination of components SEQ ID NO:1, 2, 10, linked via SEQ ID NO:6, consist of 104 aa, SEQ ID NO:1, 3, 10, linked via SEQ ID NO:6-163 aa, SEQ ID NO:1, 4, 10, linked via SEQ ID NO:6-174 aa, SEQ ID NO:1, 5, 10, linked via SEQ ID NO:6, consist of 204 aa, and have a molecular weight 10.8 kDa, pI 5.83, 17.4 kDa, pI 8.88, 18.7 kDa, pI 9.89, 21.6 kDa, pI 9.55, respectively.

Based on the calculations of the above-mentioned programme, in all types of cells an optimal half-life of any of presented in this example proteins is supported in the presence of methionine at the N-terminus of this protein. When expression of a fusion polynucleotide (variants) in any cell, a protein with methionine at the N-terminus is produced, because the translation always starts with the start codon. Further, the methionine may be cleaved, either naturally, for example, if the protein is a secreted one, in the composition of the secretory peptide, or it can be cleaved during the protein purification, as, for example, in the case of some proteins produced in cells of *Escherichia coli* and other bacteria. Thus, a fusion protein according to the invention may be with methionine at the N-terminus, or without it.

Example 2. Obtaining of Highly Purified Fusion Proteins According to the Invention with the Use of a Prokaryotic Organism Amino acid sequences of designed fusion proteins were transferred into the nucleotide ones, at the same time a codon optimization was performed for expression in *E. coli* cells using the program molbiol.ru/scripts/01_19.html and adding restriction sites flanking a gene. The designed genes were chemically synthesized.

The obtained genes are cloned in bacterial expression vector pET28a(+) at the restriction sites flanking the target genes, on the instruction to the vector.

For the creation of a producer strain cells of *E. coli* of strain BL21 Star (DE3) (Invitrogen, USA) were used, with genotype F—ompT hsdSB (rB-mB-) gal dcm rne131 (DE3), containing in the genome λDe3 lysogen and the rne131 mutation. The mutated rne gene (rne131) encodes a truncated form of RNase E, which reduces the intracellular destruction of mRNA, resulting in an increase in its enzymatic stability, lon and ompT-mutations in the genes of proteases allow to obtain non-proteolyzed recombinant proteins in large quantities.

Cells of *E. coli* strain BL21 with genotype F—ompT hsdSB (rB-mB-) gal dcm rne131 (DE3) were prepared as follows. Cells were incubated at +37° C. overnight in 5 ml of L-broth containing 1% tripton, 1% yeast extract and 1% sodium chloride. The culture was bred with a fresh L-broth 50-100 times and grown on a shaker at +37° C. to an optical density of 0.2-0.3 at a wavelength of 590 nm. Upon reaching an optical density of 0.3, the culture was diluted with a fresh L-broth to an optical density of 0.1 and grown for 30 min. 100 ml of culture were transferred in a sterile centrifuge tube, and cells were precipitated at +4° C. at 5000 g for 10 min. The supernatant was discarded, the cells were resuspended in deionized water in the original volume followed by centrifugation. The procedure of washing was repeated three times. After washing the precipitate of cells was resuspended in a small volume of deionized water and centrifuged for 30 seconds at 5000 rpm on microcentrifuge.

Transformation of competent cells was performed by the method of electroporation. For this 1 μl of tenfold diluted ligase mixture was added to 12 μl of the competent cells, mixed, and electroporation was performed on electroporator Eporator (Eppendorf, Germany) in sterile cuvettes for electroporation (Eppendorf, Germany), of a volume of 100 µl, gap 1 mm, the electric tension impulse of 1.7 kV with duration of 5 msec.

After transformation, the cells were incubated in SOC-medium (2% bacto-tripton, 0.5% of yeast extract, 10 mM NaCl, 2.5 mM KCl, 10 mM $MgCl_2$, 10 mM $MgSO_4$, 20 mM glucose) for 40 min. at +37° C. 10-100 µl of the cell suspension were plated on a selective LB-medium (Gibko B R L, USA) containing kanamycin (100 µg/ml), for selection of clones containing plasmids (producer strains).

The grown colonies of E. coli were examined for the presence of plasmids with the insert of the target gene. A clone of cells containing a plasmid DNA was considered a producer strain of the fusion protein. Thus the producer strains of fusion proteins according to the invention were obtained.

For the cultivation of the obtained producer strains a standard agar-agar LB-medium was used containing kanamycin at a concentration of 100 µg/ml and glucose at a concentration of 1% to block a non-specific expression.

Induction of expression was carried out when the cell culture reached optical density of 0.6-0.8 od units at a wavelength 600 nm. 0.2% lactose was used as the inductor (Studier, 2005).

For autoinduction expression by the method of Studier (Studier, 2005) PYP-5052 medium was used comprising 1% of peptone (Gibco, USA), 0.5% yeast extract (Gibco, USA), 50 mM $Na_2HPO_4$, 50 mM K2HPO4, 25 mM $(NH_4)_2SO_4$, 2 mM $MgSO_4$, 0.5% glycerol, 0.05% glucose and 0.2% lactose.

A single colony of the producer strain was inoculated in PYP-5052 medium containing kanamycin at a concentration of 100 µg/ml. Fermentation was carried out at +37° C. in a thermostated rotary shaker at 250 rpm min for 20 hours until no significant changes of $OD_{600}$ for 1 hour. An aliquot of cells was taken for analysis of expression of the gene encoding the fusion protein by electrophoresis in PAGE, and the remaining biomass was precipitated by centrifugation at 9000 g.

The precipitated cells were lysed with 3 cycles of sonication for 30 sec with a break of 2 min on ice. Then the destruction of the inclusion bodies was performed by incubation with a lysing buffer containing 500 mM sodium phosphate buffer, pH 8.0, 6M guanidine hydrochloride, 500 mM sodium chloride, within an hour. 8 ml of lysing buffer were added to the cells collected by centrifugation from 50 ml of culture.

A column containing Ni-NTU sepharose, pre-equilibrated with a loading buffer (500 mM sodium-phosphate buffer, pH 8.0, 8 M urea, 500 mM sodium chloride, 10 mM imidazole). The destroyed inclusion bodies were placed on the column. Further the column was washed with two volumes of loading buffer (500 mM sodium-phosphate buffer, pH 8.0, 8 M urea, 500 mM sodium chloride, 10 mM imidazole). Then the column was washed with three volumes of washing buffer (500 mM sodium-phosphate buffer, pH 8.0, 8 M urea, 500 mM sodium chloride, 30 mM imidazole). The protein was eluted with 5 ml of elution buffer (500 mM sodium-phosphate buffer, pH 8.0, 8M urea, 500 mM sodium chloride, 200 mM imidazole). Fractions of 1 ml were collected and analyzed by electrophoresis in 12% PAGE-DDS-Na, the fractions with a target protein were combined, the concentration of protein was determined according to Bradford.

Preparations of proteins were received with purity of about 97-98%, according to SDS-PAGE, the concentration of the fusion protein in each preparation was 1-2 mg/ml.

Example 3. Obtaining of Highly Purified Fusion Proteins According to the Invention with the Use of an Eukaryotic Organism 3.1. Obtaining of Highly Purified Fusion Proteins Using the Yeast Cells.

Amino acid sequences of designed fusion proteins were transferred into the nucleotide ones, at the same time a codon optimization was performed for expression in Pichia pastoris yeast cells using the program molbiol.ru/scripts/01_19.html and adding regions to obtain a secreted protein flanking a gene, according to the instruction to the vector. The designed genes were chemically synthesized.

The obtained genes are cloned in eukaryotic expression vector pHIL-S1 on the instruction to the vector.

Yeast cells were prepared for transformation. Culturing and freezing of cells of Pichia pastoris of strain SMD 1163 deficient in multiple proteases of yeast, resulting in a stability of a secreted protein, were conducted. Cells were seeded in sterile conditions on agar in the YPD medium (1%—yeast extract, 2% peptone, 2% glucose, 1 mM dithiotreitol), cultivated at 30° C., then passaged into suspension and cultured for 16 h. A part of the cells was resuspended in YPD medium with addition of 15% glycerol and frozen at −86° C. To obtain competent cells colonies of cells have been pre-grown in an agar plate in YPD medium at 30° C. for two days. Then, the content of a single colony was grown in 10 ml YPD medium at 30° C. for 16 h. The suspension was diluted in YPD to 0.2 $OD_{600}$ and the final volume of 10 ml, and the culture was grown to $OD_{600}$ 0-8 for 4 hours. The cell suspension was centrifuged for 5 min at 500 g, the supernatant was poured, resuspension was performed in 10 ml of solution I from the kit for transformation EasyComp Transformation Kit, re-centrifuged, and the precipitate was resuspended in solution I. Aliquots of competent cells—50-200 µl—were poured in sterile tubes with a volume of 1.5 ml, which were stored at a temperature of −90° C. before use.

For transformation the kit EasyComp Transformation Kit was used, being a part of the Pichia Easy Select Kit (Invitrogen), the reaction was performed according to the instruction to the kit. The resulting suspension of cells was seeded in sterile petri dish on an agar gel, prepared on the YPD medium with the addition of 1M sorbitol and ampicillin antibiotic at a final concentration of 100 µg/ml. After 3 days several dozens of colonies per cup have been obtained. Cells from grown colonies have been transferred to a cup with the MMD (minimal medium-dextrose)-agar and cultured for 2 days at 30° C.

Cells of colonies grown on the selective medium have been transferred to flasks and cultured in 5 ml of MGY medium on the shaker (250 rpm min) for 1 day until $OD_{600}$ 5. Then the cells have been precipitated by centrifugation at 3000 g for 10 min. Control of expression of the target gene was performed by the method of SDS-PAGE.

After precipitation of cells the culture medium was filtered (pore size 45 µm), then Tris-HCl pH 6.0 was added to a final concentration of 20 mM. The cultivation medium containing the fusion protein was concentrated in 5-10 times using concentrators for proteins with a molecular weight over 10 kDa of a company "Millipore".

After concentrating, the preparation of the fusion protein has been heated on a water bath to boiling (t=100° C.) and boiled for 2 minutes, then centrifuged at 4° C., 15000×g for 15 minutes.

Ion-exchanging chromatography was performed on KM-sepharose. Column with KM-sepharose was equilibrated with a buffer containing 20 mM Tris-HCl pH 6.0. The preparation of the fusion protein was applied at a speed of 60 ml/hour. The column was washed with 20 mM Tris-HCl pH 6.0; 20 mM Tris-HCl pH 6.0, 200 mM NaCl. Elution was conducted with 20 mM Tris-HCl pH 6.0, 1 M NaCl, and fractions of 1 ml were collected.

The preparation of the received fusion protein was diluted 2 times, the phosphate pH 8.0 was added to a concentration of 50 mM, and was placed on the column. After washing the column with loading buffer ballast proteins were removed by washing with a solution of 20 mM imidazole in the same buffer. Protein was eluted by a solution containing 200 mM imidazole.

As a result, preparations of the fusion protein with a purity of over 95% were obtained. The presence of bands corresponding to molecular weight of target proteins was revealed on electrophoregram. For the resulting strains a high level of expression of target proteins is characteristic.

3.2. Obtaining of Highly Purified Fusion Proteins Using Mammalian Cells.

At the N-terminus of the amino acid sequence of each fusion protein TPA (tissue-type plasminogen activator isoform 1 preproprotein [*Homo sapiens*], NCBI Reference Sequence: NP_000921.1) signal sequence was placed. Amino acid sequences of designed fusion proteins were transferred into the nucleotide ones, at the same time codon optimization was performed for expression in mammalian cells (CHO) in a manual mode, and adding restriction sites and the Kozak sequence flanking the gene. The calculated genes were chemically synthesized.

The synthesized gene was cloned in vector pcDNA3.1(+) due to instruction to the vector. A producer strain of this plasmid DNA was created based on *E. coli* DH10 B/R cells, as in protocol described in paragraph 4.1.1.

The transfection of mammalian cells by the created plasmids was carried out by calcium phosphate deposition.

For transformation of mammalian cells (CHO) by plasmid DNA the cells were cultured in 12-well plate (Costar, USA) with a seeding density of $5 \times 10^4$ cells/cm$^2$. The next day, for synchronization of cell divisions, the culture medium was replaced. Three hours later, plasmid DNA precipitated with calcium phosphate was added to the cells. To prepare the precipitate, 250 µl of solution containing 50 µg of DNA in 250 mM CaCl$_2$ was slowly mixed with 250 µl of solution (1.64% NaCl, 1.13% HEPES pH of 7.12 and 0.04% Na$_2$HPO$_4$). After 24 hours incubation at 37° C. in an atmosphere of 5% CO$_2$, the medium has been replaced with the same containing 100 µg/ml neomycin for selection of clones containing plasmid with insert of the target gene and, therefore, expressing fusion proteins, the selection has been carried out for 20 days, in the wells containing live cells, the medium has been changed (thus the previous culture medium has not been poured, but used to determine the amount of the secreted proteins by ELISA), and a day later the cells have been removed from the substrate and analyzed for the expression of the transformed genes. Analysis of the efficiency of transfection was performed on a flow cytometer Beckman Coulter EPICS XL (Beckman Coulter, USA).

The level of fusion proteins in the culture medium of the obtained stable transfectomas of line CHO was assessed using a standard solid-phase ELISA.

As a result of the clonings, stable CHO transfectomas had been obtained that have been accumulated for cryopreservation and production of an experimental batch of the fusion proteins. Productivity of created CHO transfectomas expressing fusion proteins was 420-540 µg/10$^7$ cells/day.

Cultivation of producer cells was carried out using the bioreactor BIOSTAT® Bplus and autoclaved medium IMDM with the addition of 45 g DFBS (0.5%) and 25.8 g (100 mM) of heptahydrate zinc sulphate (ZnSO$_4 \times$7H$_2$O) per 9 l of the medium. An operating mode was set: temperature 37° C., pH 6.9-7.2, oxygen concentration 50% of saturation of the air. After reaching the predetermined mode, seeding of the bioreactor was performed, for which a seed material was inoculated in aseptic conditions. Time of cultivation was 3 days.

After cultivation the culture fluid was filtered through sterile capsule "Sartopure" ("Sartorius", Germany) with a pore diameter of 1.2 µm, with a speed of 1 l/min, Then the clarified liquid was concentrated on the system of Viva Flow 200 ("Sartorius", Germany) by using a filter. Concentration was performed until the total volume was 200 ml.

A chromatographic purification was carried out in two stages, using sterile solutions. On the first stage BioLogic DuoFlow Pathfinder (Bio-Rad) system was used, with automatic collector of fractions BioFract, and semi-preparative chromatographic column YMC TriArt, 250×4.6 mm, sorbent C18. Before operating, the column was equilibrated with 200 ml of buffer (1 kg of water for injection and 1 g of trifluoroacetic acid) in manual mode through the pump of the chromatograph at the speed of 2 ml/min.

The prepared material in a volume of 200 ml was introduced into the chromatograph through the pump of the chromatograph at the speed of 0.5 ml/min. Elution was performed with buffer (2 kg of acetonitrile, 2 g of trifluoroacetic acid) at a rate of 0.5 ml per minute. A fraction was collected at the absorption maximum at 260 nm. The fraction volume was about 500 ml.

The second stage of purification was performed using gel chromatography column BioSil SEC 125-5, 300×7.8 mm. The column was equilibrated preliminarily with 0.02 M of PBS-buffer. The resulting material was introduced into the chromatograph through the pump of chromatograph at the speed of 0.5 ml/min. Elution was performed by buffer (0.6 M solution of NaCl) with a concentration gradient from 0.1 to 0.6 M. A fraction was collected with absorbance at A280 nm of not less than 3.4 optical units. The fraction was collected into vials. The volume of the resulting solution of each preparation of protein was approximately 1 l with a concentration of the fusion protein 2-2.7 mg per 1 ml.

The fusion proteins according to the invention may be obtained using other mammalian cells, e.g. HEK293, COS.

3.3. Obtaining of Highly Purified Fusion Proteins Using Plants.

The amino acid sequences of the calculated fusion proteins were transferred into nucleotide ones, at the same time codon optimization was performed for expression in *Nicotiana benthamiana* cells using the program molbiol.ru/scripts/01_19.html and adding regions flanking a gene, according to the instruction to the vector. The designed genes were chemically synthesized and cloned in eukaryotic expression vector pTRV1. It is possible to use a viral vector (for example, described in the article Komarova T. V., Skulachev M. V., Zvereva A. S., Schwartz M. A., Dorokhov Y. L., Atabekov I. G. (2006) A new virus-vector for efficient production of target proteins in plants. Biochemistry, 71(8), 1043-1049).

The resulting vector was introduced into *Agrobacterium tumefaciens* strain GV3101, which was used for infiltration of leaves of *N. benthamiana*. The resulting strain of *Agrobacterium tumefaciens* carrying the fusion gene, was cultured for 12 h at 30° C. in a shaker. Cells (1.5 ml) were precipitated by centrifugation (4000 g, 5 min), the precipitate was resuspended in buffer (1.5 ml: 10 mM $MgCl_2$, 10 mM MES (pH 5.5)), $OD_{600}$ was adjusted to 0.2. A suspension of *Agrobacterium* was syringed without a needle on the leaves of growing *N. benthamiana* plants. Maximum level of protein synthesis was observed 7-11 days after infiltration.

The expression of fusion proteins in cells of leaves of producer plants was analyzed using electrophoresis in SDS PAGE. A fragment of a leaf was triturated in buffer (10 mM KCl, 50 mM Tris pH 8.0, 5 mM $MgCl_2$, 10 mM β-mercaptoethanol, 0.4 M sucrose, 10% glycerol) on day 10 after infection. The resulting extract was subjected to centrifugation (14000 g, 10 min), the precipitate and the supernatant were analyzed using SDS-PAGE. On the electrophoretogram proteins were revealed corresponding to the molecular weight of the fusion proteins according to the invention, in the membrane fraction of cells. In control, in plants that have not undergone transformation, the corresponding proteins have not been identified. The yield of proteins was approximately 12-14% of the fraction of insoluble proteins.

Based on the obtained results, the inventive fusion proteins may be obtained using both prokaryotic and eukaryotic cell systems, highly purified preparation of each protein can be obtained using various types of protein purification. Given conditions of extraction and purification were selected experimentally and may vary in values known to the average expert in this field.

Example 4. Obtaining of Highly Purified Genetic Constructs According to the Invention The amino acid sequences of the calculated fusion proteins were transferred into nucleotide ones, at the same time codon optimization was performed for expression in mammalian cells using the program molbiol.ru/scripts/01_19.html and adding restriction sites and the Kozak sequence flanking a gene, according to the instruction to the vector. The designed genes were chemically synthesized.

4.1. Obtaining of a Plasmid DNA Coding the Fusion Protein of the Invention (Options)

4.1.1. Creation of a Producer Strain of the Plasmid DNA

The obtained genes were placed in an eukaryotic expression vector pVAX1 (Invitrogen), or pcDNA3.1+(Invitrogen) at restriction sites flanking the target genes, due to the instruction to the vector.

For the creation of producer strain, cells of *E. coli* strain DH10B/R (F-mcrA, Δ(mrr-hsdRMS-mcrBC), φ80dlacZΔM 15, ΔlacX74, deoR, recA1, endA1, araD139, Δ(ara,leu)769, galU, galKλ-, rpsL, nupG) were used which were transformed by the obtained plasmid DNA by the method of electroporation using electroporator MicroPulser (BioRad). This strain does not contain methylase, which minimizes the possibility of mutations arising in DNA, including in a cloned in the plasmid supported in this strain gene. To 12 μl of the competent cells 1 μl of a dialyzed ligase mixture was added, placed between the electrodes of a poration cell and treated with a current pulse.

After transformation, cells were placed in 1 ml of SOC-medium (2% bacto-tripton, 0.5% yeast extract, 10 mM NaCl, 2.5 mM KCl, 10 mM $MgCl_2$, 10 mM $MgSO_4$, 20 mM glucose) and incubated for 40 min at +37° C.

The identification of clones of *E. coli* cells containing the plasmid DNA obtained was conducted on the selective medium containing LB-agar, 50 μg/ml kanamycin or ampicillin, respectively.

From the grown clones the plasmid DNA was isolated. Isolation of the plasmid DNA was performed using Wizard Minipreps DNA Purification System (Promega, USA). The purified recombinant plasmid DNA was verified by sequencing.

Sequencing of the cloned fragments was performed by the method of Sanger using a set Applied Biosystems BigDye® Terminator (BDT) v3.1 Cycle Sequencing Kit (Applied Biosystems, CIIIA) according to the accompanying instruction.

For the labeling of the reaction products fluorescent dye-labeled ddNTP were used, and each ddNTP corresponded to the dye. For sequencing unlabeled plasmid-specific primers were used. A PCR reaction was conducted, then the reaction mixture was purified from free labeled ddNTP due to the instruction in the kit BigDye X-Terminator Purification Kit (Applied Biosystems, USA), and the sequencing reaction products were separated using capillary sequencer Applied Biosystems 3500/3500xL Genetic Analyzer (Applied Biosystems, USA) and reagent 3500/3500xL Genetic Analyzer Polymer "POP-6™" (Applied Biosystems, USA).

The results of the separation of the reaction products of sequencing were recorded by scanning by the laser and the detection of four fluorescent dyes included in all types of ddNTP.

The computer analysis of DNA sequences was performed using the personal computer using the programs Chromas and BioEdit. The nucleotide sequences of the investigated DNA fragments were aligned to the designed, the identity of the synthesized fragments to the calculated ones was demonstrated. As a result *E. coli* cell clones were selected containing the full sequences of the target genes in the composition of plasmids—the DNA sequences encoding the fusion proteins.

4.1.2. The Accumulation of the Plasmid DNA, Coding for the Fusion Protein (Variants)

A separate colony of *E. coli* grown on LB-agar in the Petri dish with the addition of kanamycin or ampicillin was placed in 10 ml of selective media. Cells have been grown for 12 h at +37° C. under constant stirring (250 rpm). The resulting cells were collected by centrifugation at 4000 g. Further isolation and purification of plasmid DNA was performed using the kit EndoFree Plasmid Mega Kit (Qiagen), which allows to obtain non-pyrogenic DNA. The isolated plasmid DNA was analyzed by electrophoresis in a 0.8% agarose gel, its concentration was measured using fluorometry. The yield of the plasmid DNA made up from 3.1 mg to 4.7 mg from 1 l of culture medium.

4.2. Obtaining a Vector Based on AAV Virus Encoding the Fusion Protein of the Invention (Options)

The obtained genes were placed in a vector based on AAV pAAVK-EF1Δ-MCS (System Biosciences (SBI)), on the basis of which a producer strain of the given vector was created using *E. coli* cells (RecA-), then the vector was isolated for use in mammals, all due to the instruction to the vector. The output of the vector was from 2 mg to 3.2 mg from 1 l of culture medium.

4.3. Obtaining of a Short Linear Design, Coding for a Fusion Protein of the Invention (Options)

For production of short linear construct, plasmid DNA obtained according to claim 4.1. was used. Using specific primers and PCR a fragment of plasmid DNA was amplified that contains signals for initiation of transcription, a promoter, signals of initiation of translation, the start codon, the fusion gene, 1 or 2 stop codons, transcription termination sequences, regulatory sequences.

Amplification of the mentioned sequence was performed in a total volume of 50 μl, in thin-walled polypropylene tubes with a volume of 650 μl containing 5 μl 10× Taq buffer (700 mM Tris-HCl, pH 8.6/25° C., 166 mM $(NH_4)_2SO_4$), 5 μl $MgCl_2$ (1.25 mm), 1 μl dNTP, and 31.5 μl of water, 1 ml of forward and 1 μl of reverse primer, 5 μl of plasmid DNA and 0.5 μl of Taq polymerase (Fermentas, Lithuania).

The reaction mixture was heated for 5 min at 95° C. for denaturation of DNA. To prevent evaporation, the reaction mixture of volume of 50 μl was layered with 30 μl of mineral oil Bayol F (Sigma, USA). Reaction of amplification was performed in thermal cycler S1000 Thermal Cycler (Bio-Rad, USA). 35 Cycles were carried out: 95° C.—20 seconds, 50-62° C. (depending on primers)—20 sec., 72° C.—1 min. For completing the formed DNA chains, an additional cycle was added: 5 min at 72° C.

The result of the PCR was analyzed by electrophoresis in agarose gel. If a result was positive, preparative electrophoresis was carried out.

The amplified DNA fragments were concentrated and purified by preparative electrophoresis in a 1.2% agarose gel (Gibko BRL, USA). A sample of the mixture after PCR was mixed with sixfold buffer (0.25% Bromphenol blue, 30% glycerol) (ThermoScientific, USA) and was applied to a gel, 18 μl per a well. Electrophoresis was performed in a horizontal apparatus in TAE buffer (40 mM Tris-acetate, 2 mM EDTA pH 8, 0, 0.5 μg/ml Ethidium bromide) at a voltage of 5-10 V/cm. The result of the separation of DNA was recorded in a transmitted UV light (302 nm) of transilluminator Macrovue (LKB, Sweden). The length of the amplified fragment was determined by a logarithmic dependence of DNA mobility on the length of the fragments in the marker. As markers a proprietary mix of DNA fragments "1000 bp GeneRuler DNA Ladder" (Fermentas, Lithuania) was used. The plot of agarose containing the DNA band of desired size was excised, and the DNA fragment was purified using a kit DNA&Gel Band Purification Kit (GE Healthcare, UK) in accordance with the instruction. An isolated short linear design was used in mammals.

Example 5. Identifying the Regenerative Effect of the Fusion Proteins According to the Invention Collagen-induced arthritis in rats is a model of human rheumatoid arthritis. This type of arthritis in rats was induced by introduction of native heterologous type II chicken collagen, with incomplete Freund's adjuvant. The target of this autoimmune attack is type II collagen. In collagen-induced arthritis leading role in the implementation of the effector reactions belongs to autoantibodies to collagen (a detailed description of the models: Kleinau S., 1991, Gromyko, Gritsuk 2012).

Fusion proteins according to the invention were analyzed, when one protein is introduced and when a mixture of proteins is introduced, and also when administered orally and when administered parenterally. The results were evaluated by analyzing histological sections of joints, microscopy.

5.1. The Study of the Regenerative Potential of the Drug on the Basis of One Fusion Protein (Variants) for Parenteral Administration 5.1.1. Introduction in the Periarticular Tissue After the formation of arthritis the rats were injected with a fusion protein (variants), based on the components SEQ ID NO:1, 2/3/4/5, and in some embodiments, additionally SEQ ID NO:7/8 and/or 9/10, components in the variants of the protein were presented in a different order and connected via SEQ ID NO:6 component, all the components are shown in the Sequence listing, or a mixture based on them, in the amount of 20 μg protein locally in periarticular tissues, mostly in muscle, which corresponds to the dose for humans 0.1 mg. The introduction was carried out daily for seven days. Starting from the 6th day, the morphology of joints has been analyzed, within 21 days. As a negative control saline was used. A reliable picture of a cartilage repair was obtained using all of the investigated fusion proteins, compared to control, while the best performance among the groups with the introduction of a single fusion protein was observed in the group SEQ ID NO:1-SEQ ID NO:6-SEQ ID NO:5, groups with the introduction of two fusion proteins—in the group SEQ ID NO:1-SEQ ID NO:6-SEQ ID NO:5+ SEQ ID NO:5-SEQ ID NO:6-SEQ ID NO:1, with a small gap—in the group SEQ ID NO:1-SEQ ID NO:6-SEQ ID NO:3+SEQ ID NO:1-SEQ ID NO:6-SEQ ID NO:2+SEQ ID NO:4-SEQ ID NO:6-SEQ ID NO:1+SEQ ID NO:1-SEQ ID NO:6-SEQ ID NO:5, the components are shown in the Sequence listing. The fusion proteins additionally containing component(s) of SEQ ID NO:7/8 and/or 9/10, mainly, had an effect comparable to those of proteins of similar structure that do not contain that domains, so caused regeneration of a damaged cartilage, more poorly expressed in the case of the content of two additional domains.

5.1.2. A Systemic Introduction

After the formation of arthritis the rats were injected with a fusion protein (variants), based on the components SEQ ID NO:1, 2/3/4/5, and in some embodiments, optionally SEQ ID NO:7/8 and/or 9/10, components in the variants of the protein are presented in different order and connected via SEQ ID NO:6 component, all the components are shown in the Sequence listing, or a mixture based on them, in the amount of 20-30 μg of a protein systemically—in the tail vein, which corresponds to a dose for humans of 0.2-0.3 mg. The introduction was carried out daily for seven days. Starting from the 6th day, the morphology of joints was analyzed, within 21 days. As a negative control saline was used. A reliable picture of the cartilage repair was received using all of the investigated fusion proteins, compared to control, while the best performance among the groups with the introduction of a single fusion protein was observed in the group of SEQ ID NO:5-SEQ ID NO:6-SEQ ID NO:1, groups with the introduction of two fusion proteins—in the SEQ ID NO:3-SEQ ID NO:6-SEQ ID NO:1 group (=SEQ ID NO:11) from methionine at the N-terminus of the protein (no formyl)+SEQ ID NO:5-SEQ ID NO:6-SEQ ID NO:1, with a small gap—in the group SEQ ID NO:3-SEQ ID NO:6-SEQ ID NO:1 (=SEQ ID NO:11)+SEQ ID NO:2-SEQ ID NO:6-SEQ ID NO:1+SEQ ID NO:5-SEQ ID NO:6-SEQ ID NO:1, the components are shown in the Sequence listing. When using fusion proteins containing the additional component(s) of SEQ ID NO:7/8 and/or 9/10, a little less expressed regeneration of cartilage was observed in the experiment, however, after the experiment a longer circulation of these proteins in the body was observed that may have led to the continuation of their effect on regenerative processes in the cartilage.

A less expressed regeneration of cartilage as a result of this experience was observed, compared to that in the experiment described in paragraph 5.1.1.

5.2. The Study of the Regenerative Potential of the Drug on the Basis of One Genetic Construct (Options) for Parenteral Administration 5.2.1. Introduction in the Periarticular Tissue After the formation of arthritis the rats were injected with at least 1 created genetic construct based on plasmid DNA or AAV or a linear fragment, from which in the cells of animals fusion protein was synthesized based on the components SEQ ID NO:1, 2/3/4/5, and in some embodiments, optionally SEQ ID NO:7/8 and/or 9/10, components in the variants of the protein are presented in different order and connected via SEQ ID NO:6 component, all the components shown in the Sequence listing, in the amount of 50 µg of DNA locally in periarticular tissues, mostly in muscle, which corresponds to a dose for humans of 1 mg. The introduction was carried out once every seven days, in total five times. After the third injection the morphology of joints has been analyzed, within 21 days. As a negative control the same genetic construct was used, not containing the fusion gene. A reliable picture of cartilage repair was received using all of the investigated genetic structures (DNA), compared to control, while the best performance among the groups with the introduction of the same genetic structure was observed in the groups based on the pVAX plasmid DNA, coding fusion protein SEQ ID NO:1-SEQ ID NO:6-SEQ ID NO:5, and also based on the linear construct coding fusion protein SEQ ID NO:1-SEQ ID NO:6-SEQ ID NO:4-SEQ ID NO:6-SEQ ID NO:7, with a small gap in the group based on the AAV encoding a protein SEQ ID NO:7-SEQ ID NO:6-SEQ ID NO:2-SEQ ID NO:6-SEQ ID NO:1, groups with the introduction of two genetic structures in the group on the basis of the plasmid DNA pcDNA3.1, encoding fusion proteins SEQ ID NO:1-SEQ ID NO:6-SEQ ID NO:5+SEQ ID NO:5-SEQ ID NO:6-SEQ ID NO:1 (gene with a secretion signal at the N-terminus), with a small gap in the group based on the pVAX plasmid DNA, coding fusion proteins SEQ ID NO:1-SEQ ID NO:6-SEQ ID NO:3+SEQ ID NO:1-SEQ ID NO:6-SEQ ID NO:2+SEQ ID NO:4-SEQ ID NO:6-SEQ ID NO:1+SEQ ID NO:5-SEQ ID NO:6-SEQ ID NO:1, the components shown in the Sequence listing. Genetic constructs encoding the fusion proteins additionally containing the above-mentioned fourth component, mainly, effected comparable to proteins of similar structure not containing those domains, so caused regeneration of the damaged cartilage, but more weakly expressed. The study also showed that the synthesized fusion proteins longer were detected in the serum of animals after the experiment end with the introduction of genetic constructs that encode one transport domain of SEQ ID NO:7/8/9/10. In the result of the introduction of the linearized vector slightly lower rates of regeneration were observed.

5.2.2. Systemic Introduction

After the formation of the arthritis the rats were administered with the created genetic constructs based on plasmid DNA or AAV or a linear fragment, from which in the cells of an animal a fusion protein was synthesized based on the components SEQ ID NO:1, 2/3/4/5, and in some embodiments, optionally SEQ ID NO:7/8 and/or 9/10 components in the variants of the protein are presented in different order and connected via SEQ ID NO:6 component, all the components are shown in the Sequence listing, or a mixture of such genetic structures, in the amount of 50 µg of a genetic construct systemically—in a tail vein, which corresponds to the dose for humans 1 mg. The introduction was carried out once every seven days, a total of five times. After the third injection the morphology of joints has been analyzed, within 21 days. As a negative control the same genetic construct not containing the fusion gene was used. A reliable picture of cartilage repair was received using all of the investigated genetic structures, compared to control, while the best performance among the groups with the introduction of the same genetic structure was observed in the groups based on the AAV encoding a protein SEQ ID NO:5-SEQ ID NO:6-SEQ ID NO:1, groups with the introduction of two genetic constructs—in the group on the basis of plasmid DNA encoding proteins SEQ ID NO:3-SEQ ID NO:6-SEQ ID NO:1 (being SEQ ID NO:11)+SEQ ID NO:5-SEQ ID NO:6-SEQ ID NO:1, with a small gap—in the group based on linear fragments encoding proteins SEQ ID NO:3-SEQ ID NO:6-SEQ ID NO:1 (=SEQ ID NO:11)+SEQ ID NO:2-SEQ ID NO:6-SEQ ID NO:1 (with a signal sequence at N-end)+SEQ ID NO:5-SEQ ID NO:6-SEQ ID NO:1, the components are shown in the Sequence listing. A little less expressed regeneration of cartilage was observed as a result of this experience, compared to that in the experiment described in paragraph 5.2.1.

Genetic constructs encoding the fusion proteins additionally containing component(s) SEQ ID NO:7/8 and/or 9/10, effected comparable to proteins of similar structure that do not contain those domains, so induced regeneration of the damaged cartilage, but the synthesized fusion proteins were longer detected in the serum of animals after the end of experiment.

5.3. The Study of the Regenerative Potential of the Drug on the Basis of One Fusion Protein (Variants) when Administered Orally A fusion protein (variants), presented by the components SEQ ID NO:1, 2/3/4/5, 7/8 and/or 9/10, in different sequences, connected via SEQ ID NO:6 component, the components are shown in the Sequence listing, or a mixture of such fusion proteins, was placed in enteric coating and given to rats after the formation of arthritis, in the amount of 2-3 mg of protein orally, which corresponds to the dose for a man 20-30 mg. The introduction was carried out daily for 7-30 days. Starting from the 10th day, the morphology of joints has been analyzed, within 21 days. As a negative control water was used. As a positive control a preparation of chondroitin sulfate was used, 4 mg were administered, which corresponds to a dose for humans 750 mg, 2 times a day, for 3 weeks.

A reliable picture of cartilage repair was received using all of the investigated fusion proteins, compared to control, while the best performance among the groups with the introduction of a single fusion protein was observed in groups SEQ ID NO:8-SEQ ID NO:6-SEQ ID NO:1-SEQ ID NO:6-SEQ ID NO:2/3/4/5, and SEQ ID NO:8-SEQ ID NO:6-SEQ ID NO:2/3/4/5-SEQ ID NO:6-SEQ ID NO:1, groups with the introduction of two fusion proteins—in the group SEQ ID NO:10-SEQ ID NO:6-SEQ ID NO:5-SEQ ID NO:1+SEQ ID NO:1-SEQ ID NO:6-SEQ ID NO:2-SEQ ID NO:6-SEQ ID NO:9, the components are shown in the Sequence listing. It is revealed that when in conjunction with a three-component or a four-component (including transport domain) a two-component fusion protein (not including transport domain) is used, the difference in the results is insignificant in comparison with the introduction of a protein from three or four components.

Regeneration of cartilage was observed as a result of this experience, comparable to that observed in the experiment 5.1.1. In addition, a prolonged circulation of fusion proteins containing the transport domain was observed, in the blood. The use of a particular enteric coating does not affect the results of the study.

Also a similar study was conducted on rabbits, to whom a surgical tear of the meniscus was introduced. The results of that study correlate with the results obtained in the study on the model of collagen-induced arthritis in rats.

So, the possibility is proved of obtaining fusion proteins, polynucleotides, genetic constructs, producers, drugs for the regeneration of cartilage (all versions). It is also shown that the developed fusion proteins have a significant regenerative effect on the damaged cartilage, both directly imposed and with the introduction of genetic constructs encoding them. In all studies an increase in the number of chondrocytes in previously damaged joints was observed, which probably caused the regeneration of cartilage. This allows to conclude that in other types of cartilage defects the proposed invention (embodiments) will allow for their regeneration.

The invention claimed is:

1. A fusion protein comprising a ligand to matrilin (MATN1) set forth as the amino acid sequence of SEQ ID NO: 1 and a growth factor selected from the group consisting of Epidermal Growth Factor (EGF), Transforming Growth Factor (TGF), Fibroblast Growth Factor (FGF), and Insulin-like Growth Factor (IGF) set forth as the amino acid sequence of SEQ ID NO: 2, 3, 4 or 5, respectively, wherein the ligand to MATN1 and the growth factor are connected via a flexible linker set forth as the amino acid sequence of SEQ ID NO: 6.

2. The fusion protein of claim 1, which is further connected via a flexible linker set forth as the amino acid sequence of SEQ ID NO: 6 to at least one of: (i) the Fc-fragment of an antibody set forth as the amino acid sequence of SEQ ID NO: 7 or a polypeptide which binds with FcRn set forth as the amino acid sequence of SEQ ID NO: 8, and (ii) transferrin set forth as the amino acid sequence of SEQ ID NO: 9 or a fragment thereof set forth as the amino acid sequence of SEQ ID NO: 10, wherein the connection between (i) and (ii) is also via the flexible linker.

3. A preparation for regeneration of cartilage, containing at least one fusion protein of claim 1 as an active agent in an effective amount, and a physiologically acceptable carrier and a buffer solution, wherein the preparation is for parenteral administration.

4. A preparation for regeneration of cartilage, containing at least one fusion protein of claim 2 as an active agent in an effective amount, and a physiologically acceptable carrier and a buffer solution, wherein the preparation is for parenteral administration.

5. A preparation for regeneration of cartilage, containing at least one fusion protein of claim 2 as an active agent in an effective amount, and a physiologically acceptable carrier and a buffer solution, wherein the preparation is enclosed in an enteric coating for oral administration.

6. A preparation for regeneration of cartilage containing:
as an active agent:
an effective amount of at least one fusion protein of claim 1; and
an effective amount of at least one fusion protein of claim 1 which is further connected via a flexible linker set forth as the amino acid sequence of SEQ ID NO: 6 to at least one of: (i) the Fc-fragment of an antibody set forth as the amino acid sequence of SEQ ID NO: 7 or a polypeptide which binds with FcRn set forth as the amino acid sequence of SEQ ID NO: 8, and (ii) transferrin set forth as the amino acid sequence of SEQ ID NO: 9 or a fragment thereof set forth as the amino acid sequence of SEQ ID NO: 10, wherein the connection of between (i) and (ii) is also via the flexible linker;
a physiologically acceptable carrier; and
a buffer solution,
wherein the preparation is for parenteral administration.

* * * * *